(12) United States Patent
Jedwab et al.

(10) Patent No.: US 11,766,210 B2
(45) Date of Patent: Sep. 26, 2023

(54) METHODS AND DEVICES FOR DETERMINING SIGNAL QUALITY FOR A SWALLOWING IMPAIRMENT CLASSIFICATION MODEL

(71) Applicant: SOCIETE DES PRODUITS NESTLE S.A., Vevey (CH)

(72) Inventors: Michael Reuben Jedwab, Lausanne (CH); Juha M. Kortelainen, Tampere (FI); Rajat Mukherjee, Cambridge, MA (US); Harri Polonen, Tampere (FI)

(73) Assignee: Societe des Produits Nestle S.A., Vevey (CH)

( * ) Notice: Subject to any disclaimer, the term of this patent is extended or adjusted under 35 U.S.C. 154(b) by 318 days.

(21) Appl. No.: 16/636,449

(22) PCT Filed: Jul. 31, 2018

(86) PCT No.: PCT/EP2018/070649
§ 371 (c)(1),
(2) Date: Feb. 4, 2020

(87) PCT Pub. No.: WO2019/030046
PCT Pub. Date: Feb. 14, 2019

(65) Prior Publication Data
US 2020/0170562 A1    Jun. 4, 2020

Related U.S. Application Data

(60) Provisional application No. 62/541,943, filed on Aug. 7, 2017.

(51) Int. Cl.
*A61B 5/00* (2006.01)
*G06F 3/01* (2006.01)
*G06F 17/18* (2006.01)

(52) U.S. Cl.
CPC .......... *A61B 5/4205* (2013.01); *A61B 5/7203* (2013.01); *A61B 5/7264* (2013.01);
(Continued)

(58) Field of Classification Search
CPC ... A61B 5/4205; A61B 5/7203; A61B 5/7264; A61B 5/7435; A61B 5/11; A61B 5/6822;
(Continued)

(56) References Cited

U.S. PATENT DOCUMENTS

2008/0269646 A1    10/2008 Chau et al.
2010/0160833 A1    6/2010 Chau et al.
(Continued)

FOREIGN PATENT DOCUMENTS

JP    2008502386 A    1/2008

OTHER PUBLICATIONS

Merey, Celeste, et. al. "Quantitative classification of pediatric swallowing through accelerometry" 2012, Journal of NeuroEngineering and Rehabilitation, 9 (34) (Year: 2012).*
(Continued)

*Primary Examiner* — Patrick Fernandes
*Assistant Examiner* — Anna Roberts
(74) *Attorney, Agent, or Firm* — K&L Gates LLP

(57) ABSTRACT

A device can screen swallowing safety and swallowing efficiency. The device includes a processor configured to receive accelerometry data, determine a an A-P and S-I signal summed spectrogram from the accelerometry data, and perform one or more of identifying a missing swallow, identifying that the data was clipped from the start, identifying that the data was clipped from the end, or identifying that the data contains noise. The device can have a user
(Continued)

interface configured to provide one or more outputs including at least one of audio or graphics based on these identifications. If the data does not contain these signal quality issues, the device can compare the data against preset classification criteria defined for each of swallowing safety and swallowing efficiency and thus classify each of the swallowing events with a swallowing safety classification and a swallowing efficiency classification.

17 Claims, 17 Drawing Sheets

(52) U.S. Cl.
CPC ............ *A61B 5/7435* (2013.01); *G06F 3/011* (2013.01); *G06F 3/017* (2013.01); *G06F 17/18* (2013.01); *A61B 2562/0219* (2013.01)

(58) Field of Classification Search
CPC ... A61B 5/1121; A61B 5/1123; A61B 5/1124; A61B 5/7267; A61B 5/7221; A61B 5/7207; A61B 2562/0219; G06F 3/011; G06F 3/017; G06F 17/18; G16H 20/40; G16H 40/63; G16H 50/20; G16H 50/70
See application file for complete search history.

(56) References Cited

U.S. PATENT DOCUMENTS

| | | | |
|---|---|---|---|
| 2013/0184538 A1* | 7/2013 | Lee ...................... | A61B 5/1123 600/301 |
| 2019/0038208 A1* | 2/2019 | Mohammadi .......... | G16H 50/20 |

OTHER PUBLICATIONS

Dudik, Joshua, et. al. "Dysphagia Screening: Contributions of Cervical Auscultation Signals and Modern Signal-Processing Techniques" 2015, IEEE Trans Hum Mach Syst, 45 (4) (Year: 2015).*
Welinitz, Arne, et. al. "Fluid Intake Recognition using Inertial Sensors" 2019, iWOAR Proceedings of the 6th international Workshop on Sensor-based Activity Recognition and Interaction (Year: 2019).*
Dudik, Joshua, et. al. "A comparative analysis of DBSCAN, K-means, and quadratic variation algorithms for automatic identification of swallows from swallowing accelerometry signals" 2015, Computers in Biology and Medicine, 59, 10-18 (Year: 2015).*
Prodeus, A.M., et. al. "Kurtosis and Normalized Variance as Measures of Speech Signals Clipping Value" 2019, Electronics and Control Systems, 4 (62) (Year: 2019).*
Damouras, Sotirios, et. al. "An Online Swallow Detection Algorithm Based on the Quadratic Variation of Dual-Axis Accelerometry" Jun. 2010, IEEE Transactions on Signal Processing, vol. 58, No. 6 (3352-3359) (Year: 2010).*
Lee et al. "Effects of liquid stimuli on dual-axis swallowing accelerometry signals in a healthy population" BioMedical Engineering OnLine, 2010, vol. 9, No. 7, 14 pages.
Merey et al. "Quantitative classification of pediatric swallowing through accelerometry" Journal of NeuroEngineering and Rehabilitation, 2012, vol. 9, No. 34, 8 pages.
Dudik et al. "Dysphagia Screening: Contributions of Cervical Auscultation Signals and Modern Signal-Processing Techniques" IEEE Transactions on Human-Machine Systems, Aug. 2015, vol. 45, No. 4, pp. 465-477.
Japan Patent Office Communication for Application No. 2020-504147, Dispatch No. 346846, Dispatch Date Jul. 26, 2022, 15 pages.

* cited by examiner

METHODS AND DEVICES FOR DETERMINING SIGNAL QUALITY FOR A SWALLOWING IMPAIRMENT CLASSIFICATION MODEL

CROSS REFERENCE TO RELATED APPLICATIONS

The present application is a National Stage of International Application No. PCT/EP2018/070649, filed on Jul. 31, 2018, which claims priority to U.S. Provisional Patent Application No. 62/541,943, filed on Aug. 7, 2017, the entire contents of which are being incorporated herein by reference.

BACKGROUND

The present disclosure relates to methods and devices that determine quality of an accelerometry signal for a swallowing impairment classification model that screens swallowing safety and swallowing efficiency. More specifically, an integrated device uses parameters acquired from signal preprocessing and/or swallow segmentation of accelerometry data to identify an accelerometry signal as 1) a missing swallow, 2) clipped from start swallow, 3) clipped from end swallow or 4) noisy signal.

Dysphagia is characterized by impaired involuntary motor control of a swallowing process and can cause "penetration" which is the entry of foreign material into the airway. The airway invasion can be accompanied by "aspiration" in which the foreign material enters the lungs and can lead to serious health risks.

The three phases of swallowing activity are oral, pharyngeal and esophageal. The pharyngeal phase is typically compromised in patients with dysphagia. The impaired pharyngeal phase of swallowing in dysphagia is a prevalent health condition (38% of the population above 65 years) and may result in prandial aspiration (entry of food into the airway) and/or pharyngeal residues, which in turn can pose serious health risks such as aspiration pneumonia, malnutrition, dehydration, and even death. Swallowing aspiration can be silent (i.e., without any overt signs of swallowing difficulty such as cough), especially in children with dysphagia and patients with acute stroke, rendering detection via clinical perceptual judgement difficult.

Screening for dysphagia is a process used to identify those patients who are at risk for aspiration, malnutrition or dehydration and who need a further clinical assessment by a professional trained in the diagnosis and management of dysphagia. Screening alone is inadequate to detect the presence or absence of dysphagia or aspiration; however, patients with swallowing problems should be identified as early as possible to allow more severely impaired patients to be managed without delay. Screening for dysphagia is essential on initial admission to develop treatment plans, determine if food and fluids should be withheld from the patient, and whether a nasogastric (NG) tube will be necessary, as well as other issues related to eating and nutrition, aspirating, and swallowing food.

Although a wide variety of swallow screening and assessment tests are available for use, none have acceptable sensitivity and specificity to ensure accurate detection of dysphagia.

Several reviews have shown a lack of consensus regarding the best screening instrument to use. Most bedside swallowing examinations have been shown to lack sufficient sensitivity to be used for screening purposes, regardless of the patient populations examined. No bedside screening protocol has been shown to provide adequate predictive value for the presence of aspiration. Several individual exam components have demonstrated reasonable sensitivity, but reproducibility and consistency of these protocols was not established. Dysphagia screening validation studies reported in the literature have a number of serious limitations. It is also important to note that between one-third and one-half of patients who aspirate following stroke are silent aspirators (i.e., penetration of food below the level of the true vocal cords, without cough or any outward sign of difficulty).

In 2010, the Joint Commission™ (which accredits health care organizations and programs in the United States) withdrew the dysphagia screening performance standard for acute stroke because the National Quality Forum™ could not endorse the standard, stating that there are "no standards for what constitutes a valid dysphagia screening tool, and no clinical trials have been completed that identify the optimal swallow screening." Dysphagia screening was removed from the "Get with the Guidelines" stroke guidelines. However, removal from the Joint Commission™ recommendations does not mean that screenings should not be performed; indeed the Joint Commission™ recommends further research to improve dysphagia screening methods.

Videofluoroscopic swallowing study (VFSS) has long been regarded as the clinical reference method (gold standard) in the assessment of dysphagia. VFSS dynamically visualizes the oral, pharyngeal and esophageal phases of swallowing. VFSS provides a comprehensive assessment of swallowing, determining not only whether the patient is aspirating but also enabling an analysis of the pathophysiological mechanisms leading to aspiration. Penetration and aspiration are most commonly graded according to the rating scale of Rosenbek, et al. However, VFSS requires specialized equipment and staff and involves exposure to radiation. Some patients are poorly suited to VFSS, such as those who are medically fragile and may be unable to be transported to radiology (e.g., complex acute stroke patients and ICU patients).

Fiber-optic endoscopic evaluation of swallowing (FEES) is another instrumental assessment of swallowing, using a flexible nasolaryngoscope which is passed through the nares, over the velum into the pharynx. Recent studies suggest that FEES is a safe, reliable and predictive tool for dysphagia assessment patients with acute stroke. The main disadvantage of FEES compared to VFSS is that not the whole swallowing act is covered and furthermore the endoscopic view is impaired intradeglutitively for a short moment. FEES is now probably the most frequently used tool for objective dysphagia assessment in Germany. It allows evaluation of the efficacy and safety of swallowing, determination of appropriate feeding strategies, and assessment of the efficacy of different swallowing maneuvers. AHA/ASA-Endorsed Practice Guidelines Management of Adult Stroke Rehabilitation Care recommends considering fiber-optic endoscopic examination of swallowing (FEES) as an alternative to VFSS.

A clinical (or bedside) swallowing evaluation (CSE) is a behavioral assessment of swallowing function usually performed by an SLP (Speech Language Pathologist). This evaluation is a practical method of assessment but has limitations and relies on subjective evaluation by skilled clinicians. 40% of variables typically used in a CSE are unsupported by data, and only 44% of the measures typically used by clinicians have exhibited adequate intra- and inter judge reliability.

Bedside screening tests for dysphagia are safe, relatively straightforward, and easily repeated but have variable sensitivity (42% to 92%), specificity (59% to 91%), and inter-rater reliability (k 0 to 1.0). They are also poor at detecting silent aspiration. The accuracy of the WST (Water Swallow Test), which is currently the tool used most often to screen patients at risk of dysphagia in clinical settings, has been repeatedly questioned during recent years. Two meta-analyses conducted by Ramsey, et al. and Bours, et al. suggested that when compared to VFSS or FEES, the sensitivity of the WST for detecting aspiration is markedly below 80% in nearly all reviewed studies. This observation also applies to specificity and also negative and positive predictive values.

Most swallow screening approaches involve observations of voice quality, voluntary cough function, speech clarity, tongue function and swallows of water or other stimuli. The clinicians administering the test are expected to identify abnormalities in these parameters, including post-swallow cough or wet voice. Blinded comparison of results between a standardized swallowing screening protocol in which clinicians were asked to judge these parameters and simultaneous VFSS revealed that none of the screening parameters were adequate for decision-making, for detecting pharyngeal dysphagia, or for detecting laryngeal penetration and aspiration.

The Toronto Bedside Swallowing Screening Test (TOR-BSST) reports a sensitivity of 91% (95% CI, 71.9-98.7) and a specificity of 67% (95% CI, 49.0-81.4). The limitations of this test include questionable feasibility, limited operational definitions, a small validation sample with only 20% of subjects (n=68) in the trial contributing to validation, and extended time between the screening and reference test. This last limitation is especially important in the stroke population due to the rapid evolution of dysphagia, especially in the acute period. The Gugging Swallow Screen (GUSS) was validated in a small study in acute stroke patients (delivered by SLPs in 19 patients and by nurses in 30 patients) and showed excellent sensitivity of 100% and specificity 50% for SLP validation and sensitivity of 100% and specificity of 69% in validation with nurses. The limitations include a lack of reliability information for nurses, unknown feasibility given complexity (the test consists of two parts including 3 sequentially performed subtests, starting with semisolid food, then liquids, and finally solid textures), and a small sample size in the validation study.

Notably, most screening methods have been developed for and tested in stroke patients. The clinical usability and accuracy of these methods in other populations at risk of dysphagia can be questioned. For example, the results of a self-administered survey from 836 certified SLPs from all fifty states in the U.S.A. showed that even though respondents reported being regularly involved in swallowing assessment and the provision of care for those who have received mechanical ventilation, the majority of SLP diagnostic evaluations (60%; 95% CI=59-62%) were performed using clinical techniques with uncertain accuracy.

Considering the limitations of the clinical swallowing examination, the CSE cannot be used as a reference method for the validation of new screening tools, leaving VFSS and FEES as only the only valid reference standards of choice.

The development of a fully automated, accurate swallowing screening tool remains an elusive challenge.

SUMMARY

In an embodiment, the present disclosure provides a device for screening swallowing safety and swallowing efficiency. The device comprises: a processor configured to receive accelerometry data, determine an A-P and S-I signal summed spectrogram from the accelerometry data, and perform at least one method selected from the group consisting of (i) determining a signal variance of the accelerometry data as a function of time, as a summed power over a specific frequency range of the spectrogram, and comparing the signal variance to a first threshold value, (ii) determining a normalized variance signal from the spectrogram, selecting a beginning portion of the normalized variance signal, and comparing values of the beginning portion of the normalized variance signal to a second threshold value, (iii) determining a normalized variance signal from the spectrogram, selecting an end portion of the normalized variance signal, and comparing values of the end portion of the normalized variance signal to a third threshold value, and (iv) determining a summed power spectral density of both S-I and A-P signals as an average of the spectrogram over a whole bolus length and applying spectral entropy for the summed power spectral density (PSD) of both S-I and A-P signals for comparison to a fourth threshold value. The device comprises a user interface configured to provide one or more outputs comprising at least one of audio or graphics based on one or more results of the at least one method.

In an embodiment, the at least one method performed by the processor is real-time relative to receipt of the corresponding accelerometry data.

In an embodiment, the device further comprises an accelerometer communicatively connected to the processor to provide the accelerometry data.

In an embodiment, the at least one method comprises determining a signal variance of the accelerometry data as a function of time, as a summed power over a specific frequency range of the spectrogram, and comparing the signal variance to a first upper threshold value; and the one or more outputs indicate a missing swallow for the corresponding accelerometry data. The processor can be configured to cease processing of the corresponding accelerometry data in response to identification of the missing swallow.

In an embodiment, the at least one method comprises determining a normalized variance signal from the spectrogram, selecting a beginning portion of the normalized variance signal, and comparing values of the beginning portion of the normalized variance signal to a second threshold value; and the one or more outputs indicate that the corresponding accelerometry data was clipped from the start. The processor can be configured to cease processing of the corresponding accelerometry data in response to identification of the corresponding accelerometry data being clipped from the start.

In an embodiment, the at least one method comprises determining a normalized variance signal from the spectrogram, selecting an end portion of the normalized variance signal, and comparing values of the end portion of the normalized variance signal to a third threshold value; and the one or more outputs indicate that the corresponding accelerometry data was clipped from the end. The processor can be configured to cease processing of the corresponding accelerometry data in response to identification of the corresponding accelerometry data being clipped from the end.

In an embodiment, the at least one method comprises determining a summed power spectral density of both S-I and A-P signals as an average of the spectrogram over a whole bolus length and applying spectral entropy for the summed power spectral density (PSD) of both S-I and A-P signals for comparison to a fourth threshold value; and the one or more first output indicate that the corresponding accelerometry data comprises noise. The processor can be configured to cease processing of the corresponding accelerometry data in response to identification of the noise in the corresponding accelerometry data.

In another embodiment, the present disclosure provides a device for screening swallowing safety and swallowing efficiency. The device comprises: a processor configured to receive accelerometry data, determine an A-P and S-I signal summed spectrogram from the accelerometry data, determine a signal variance of the accelerometry data as a function of time, as a summed power over a specific frequency range of the spectrogram, compare the signal variance to a first threshold value, select a beginning portion of the normalized variance signal and compare values of the beginning portion of the normalized variance signal to a second threshold value, select an end portion of the normalized variance signal and compare values of the end portion of the normalized variance signal to a third threshold value, and determine a summed power spectral density of both S-I and A-P signals as an average of the spectrogram over a whole bolus length and apply spectral entropy for the summed power spectral density (PSD) of both S-I and A-P signals for comparison to a fourth threshold value. The processor is further configured to react to the accelerometry data not exceeding the first, second, third and fourth threshold values by comparing the accelerometry data against preset classification criteria defined for each of swallowing safety and swallowing efficiency and classify each of the first plurality of swallowing events with a swallowing safety classification and a swallowing efficiency classification based at least partially on the comparing of the swallowing data against the preset classification criteria. The device further comprises a user interface configured to provide one or more outputs comprising at least one of audio or graphics that identify the swallowing safety classification and the swallowing efficiency classification for each of the first plurality of swallowing events.

In an embodiment, the device further comprises an accelerometer communicatively connected to the processor to provide the accelerometry data.

In an embodiment, the swallowing safety classification is identified from at least two predetermined swallowing safety classifications, and the swallowing efficiency classification is identified from at least two predetermined swallowing efficiency classifications. The at least two predetermined swallowing safety classifications comprise a first swallowing safety classification indicative of a safe event and a second swallowing safety classification indicative of an unsafe event, and the at least two predetermined swallowing efficiency classifications comprise a first swallowing efficiency classification indicative of an efficient event and a second swallowing efficiency classification indicative of an inefficient event. The one or more outputs comprise at least one icon displayed on the user interface, at least a portion of the at least one icon is a first color for the first swallowing safety classification or a second color different than the first color for the second swallowing safety classification, at least a portion of the at least one icon is a third color for the first swallowing efficiency classification or a fourth color different than the third color for the second swallowing efficiency classification, and at least a portion of the at least one icon is a fifth color if any of the first, second, third and fourth threshold values were exceeded. Preferably the first and third colors are the same color, and the second and fourth colors are the same color.

In another embodiment, the present disclosure provides a method of screening swallowing safety and swallowing efficiency. The method comprises: receiving, on a device comprising a processor, accelerometry data for a swallowing event executed by an individual; determining, on the device, an A-P and S-I signal summed spectrogram from the accelerometry data; performing, on the device, at least one method selected from the group consisting of (i) determining a signal variance of the accelerometry data as a function of time, as a summed power over a specific frequency range of the spectrogram, and comparing the signal variance to a first threshold value, (ii) determining a normalized variance signal from the spectrogram, selecting a beginning portion of the normalized variance signal, and comparing values of the beginning portion of the normalized variance signal to a second threshold value, (iii) determining a normalized variance signal from the spectrogram, selecting an end portion of the normalized variance signal, and comparing values of the end portion of the normalized variance signal to a third threshold value, and (iv) determining a summed power spectral density of both S-I and A-P signals as an average of the spectrogram over a whole bolus length and applying spectral entropy for the summed power spectral density (PSD) of both S-I and A-P signals for comparison to a fourth threshold value. The method further comprises producing, from the device, one or more outputs comprising at least one of audio or graphics based on one or more results of the at least one method.

In an embodiment, the method comprises transmitting the first accelerometry data to the device from an accelerometer communicatively connected to the device.

In an embodiment, the at least one method comprises determining a signal variance of the accelerometry data in function of time, as a summed power over a specific frequency range of the spectrogram, and comparing the signal variance to a first upper threshold value; and the one or more outputs indicate a missing swallow for the corresponding accelerometry data. The method can comprise the processor ceasing processing of the corresponding accelerometry data in response to identification of the missing swallow.

In an embodiment, the at least one method comprises determining a normalized variance signal from the spectrogram, selecting a beginning portion of the normalized variance signal, and comparing values of the beginning portion of the normalized variance signal to a second threshold value; and the one or more outputs indicate that the corresponding accelerometry data was clipped from the start. The method can comprise the processor ceasing processing of the corresponding accelerometry data in response to identification of the corresponding accelerometry data being clipped from the start.

In an embodiment, the at least one method comprises determining a normalized variance signal from the spectrogram, selecting an end portion of the normalized variance signal, and comparing values of the end portion of the normalized variance signal to a third threshold value; and the one or more outputs indicate that the corresponding accelerometry data was clipped from the end. The method can comprise the processor ceasing processing of the corresponding accelerometry data in response to identification of the corresponding accelerometry data being clipped from the end.

In an embodiment, the at least one method comprises determining a summed power spectral density of both S-I and A-P signals as an average of the spectrogram over a whole bolus length and applying spectral entropy for the summed power spectral density (PSD) of both S-I and A-P signals for comparison to a fourth threshold value; and the one or more first output indicate that the corresponding accelerometry data comprises noise. The method can comprise the processor ceasing processing of the corresponding accelerometry data in response to identification of the noise in the corresponding accelerometry data.

In another embodiment, the present disclosure provides a method of screening swallowing safety and swallowing efficiency. The method comprises: receiving, on a device comprising a processor, accelerometry data for a swallowing event executed by an individual; determining, on the device, an A-P and S-I signal summed spectrogram from the accelerometry data; determining, on the device, a signal variance of the accelerometry data as a function of time, as a summed power over a specific frequency range of the spectrogram, and comparing the signal variance to a first threshold value; determining, on the device, a normalized variance signal from the spectrogram; selecting a beginning portion of the normalized variance signal; comparing, on the device, values of the beginning portion of the normalized variance signal to a second threshold value; selecting an end portion of the normalized variance signal; comparing, on the device, values of the end portion of the normalized variance signal to a third threshold value; determining, on the device, a summed power spectral density of both S-I and A-P signals as an average of the spectrogram over a whole bolus length and applying spectral entropy for the summed power spectral density (PSD) of both S-I and A-P signals for comparison to a fourth threshold value. In response to the accelerometry data not exceeding the first, second, third and fourth threshold values, the device compares the accelerometry data against preset classification criteria defined for each of swallowing safety and swallowing efficiency and classify each of the first plurality of swallowing events with a swallowing safety classification and a swallowing efficiency classification based at least partially on the comparing of the swallowing data against the preset classification criteria. The method comprises producing, from the device, one or more outputs comprising at least one of audio or graphics that identify the swallowing safety classification and the swallowing efficiency classification for each of the first plurality of swallowing events.

In an embodiment, the swallowing safety classification is identified from at least two predetermined swallowing safety classifications, and the swallowing efficiency classification is identified from at least two predetermined swallowing efficiency classifications. The at least two predetermined swallowing safety classifications comprise a first swallowing safety classification indicative of a safe event and a second swallowing safety classification indicative of an unsafe event, and the at least two predetermined swallowing efficiency classifications comprise a first swallowing efficiency classification indicative of an efficient event and a second swallowing efficiency classification indicative of an inefficient event. The one or more outputs comprise at least one icon displayed on the user interface, at least a portion of the at least one icon is a first color for the first swallowing safety classification or a second color different than the first color for the second swallowing safety classification, at least a portion of the at least one icon is a third color for the first swallowing efficiency classification or a fourth color different than the third color for the second swallowing efficiency classification, and at least a portion of the at least one icon is a fifth color if any of the first, second, third and fourth threshold values were exceeded. Preferably the first and third colors are the same color, and the second and fourth colors are the same color.

DETAILED DESCRIPTION

Definitions

Figure 1:
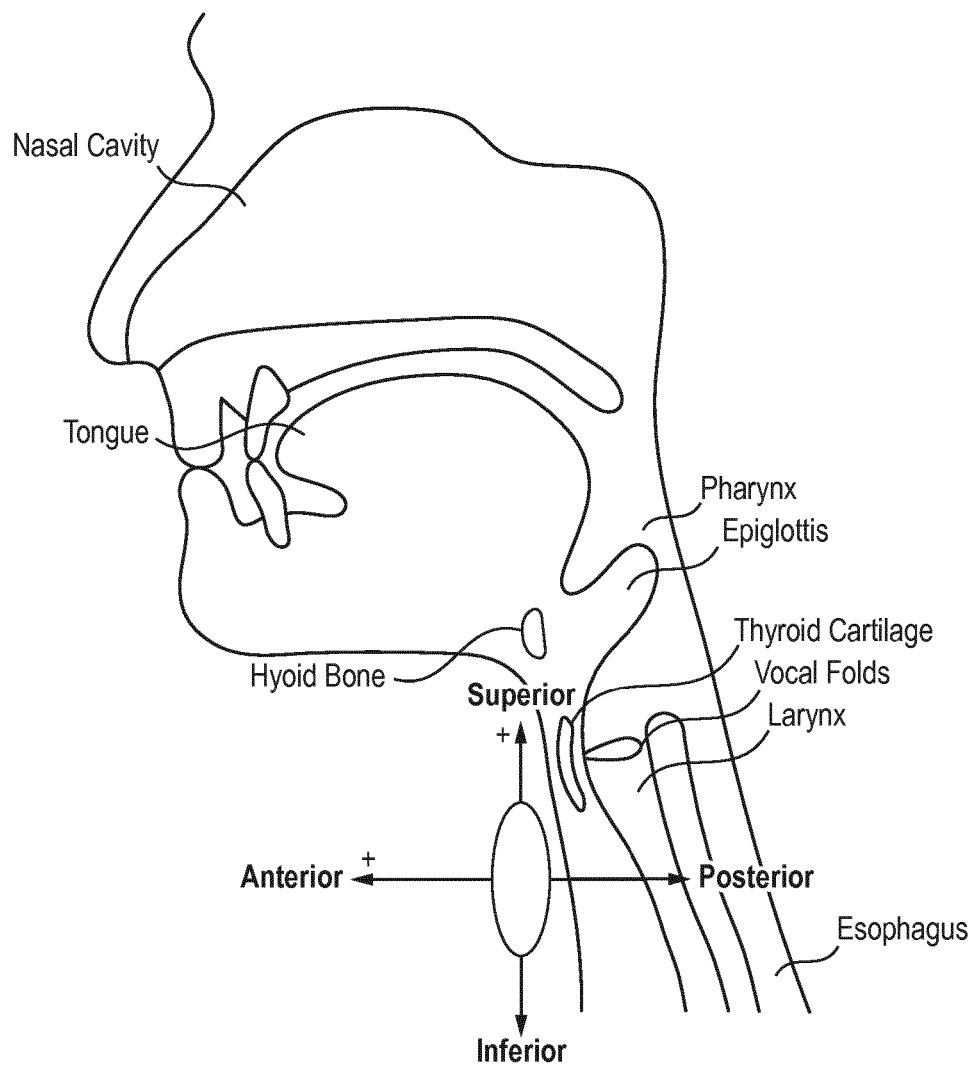
FIG. 1 is diagram showing the axes of acceleration in the anterior-posterior and superior-inferior directions.

Some definitions are provided hereafter. Nevertheless, definitions may be located in the "Embodiments" section below, and the above header "Definitions" does not mean that such disclosures in the "Embodiments" section are not definitions.

As used in this disclosure and the appended claims, the singular forms "a," "an" and "the" include plural referents unless the context clearly dictates otherwise. As used herein, "about" is understood to refer to numbers in a range of numerals, for example the range of −10% to +10% of the referenced number, preferably −5% to +5% of the referenced number, more preferably −1% to +1% of the referenced number, most preferably −0.1% to +0.1% of the referenced number. Moreover, all numerical ranges herein should be understood to include all integers, whole or fractions, within the range.

The words "comprise," "comprises" and "comprising" are to be interpreted inclusively rather than exclusively. Likewise, the terms "include," "including" and "or" should all be construed to be inclusive, unless such a construction is clearly prohibited from the context. A disclosure of a device "comprising" several components does not require that the components are physically attached to each other in all embodiments.

Nevertheless, the devices disclosed herein may lack any element that is not specifically disclosed. Thus, a disclosure of an embodiment using the term "comprising" is also a disclosure of embodiments "consisting essentially of" and "consisting of" the components identified. Similarly, the methods disclosed herein may lack any step that is not specifically disclosed herein. Thus, a disclosure of an embodiment using the term "comprising" is also a disclosure of embodiments "consisting essentially of" and "consisting of" the steps identified.

The term "and/or" used in the context of "X and/or Y" should be interpreted as "X," or "Y," or "X and Y." Where used herein, the terms "example" and "such as," particularly when followed by a listing of terms, are merely exemplary and illustrative and should not be deemed to be exclusive or comprehensive. Any embodiment disclosed herein can be combined with any other embodiment disclosed herein unless explicitly stated otherwise.

Numerical adjectives, such as "first" and "second," are merely used to distinguish components. These numerical adjectives do not imply the presence of other components, a relative positioning, or any chronological implementation. In this regard, the presence of "second accelerometry data" does not imply that "first accelerometry data" is necessarily present. Further in this regard, "second accelerometry data" can be obtained and/or used before, after, or simultaneously with any "first accelerometry data."

As used herein, a "bolus" is a single sip or mouthful or a food or beverage. As used herein, "aspiration" is entry of food or drink into the trachea (windpipe) and lungs and can occur during swallowing and/or after swallowing (post-deglutitive aspiration). Post-deglutitive aspiration generally occurs as a result of pharyngeal residue that remains in the pharynx after swallowing.

As used herein, "swallowing safety" means the amount of a dose of beverage in a swallowing event that reaches the stomach relative to the amount of the dose of beverage that reaches the lungs, if any. "Swallowing efficiency" means how much beverage residue is left behind in the throat and/or by the lungs if any, after a swallowing event relative to the total dose of the beverage.

As used herein, "real-time" means the output in provided within ten seconds of the in a swallowing event, preferably within five seconds, more preferably within two seconds, most preferably within one second.

Embodiments

An aspect of the present disclosure is a device for screening swallowing safety and swallowing efficiency. Another aspect of the present disclosure is a method of screening swallowing safety and swallowing efficiency.

In some embodiments, the method and the device can be employed in one or more of the apparatus and/or the method for detecting aspiration disclosed in U.S. Pat. No. 7,749,177 to Chau et al., the method and/or the system of segmentation and time duration analysis of dual-axis swallowing accelerometry signals disclosed in U.S. Pat. No. 8,267,875 to Chau et al., the system and/or the method for detecting swallowing activity disclosed in U.S. Pat. No. 9,138,171 to Chau et al., or the method and/or the device for swallowing impairment detection disclosed in U.S. Patent App. Publ. No. 2014/0228714 to Chau et al., each of which is incorporated herein by reference in its entirety.

As discussed in greater detail hereafter, the device may include a sensor configured to produce signals indicating swallowing activities (e.g., a dual axis accelerometer). The sensor may be positioned externally on the neck of a human, preferably anterior to the cricoid cartilage of the neck. A variety of means may be applied to position the sensor and to hold the sensor in such position, for example double-sided tape. Preferably the positioning of the sensor is such that the axes of acceleration are aligned to the anterior-posterior and super-inferior directions, as shown in FIG. 1.

Figure 2:
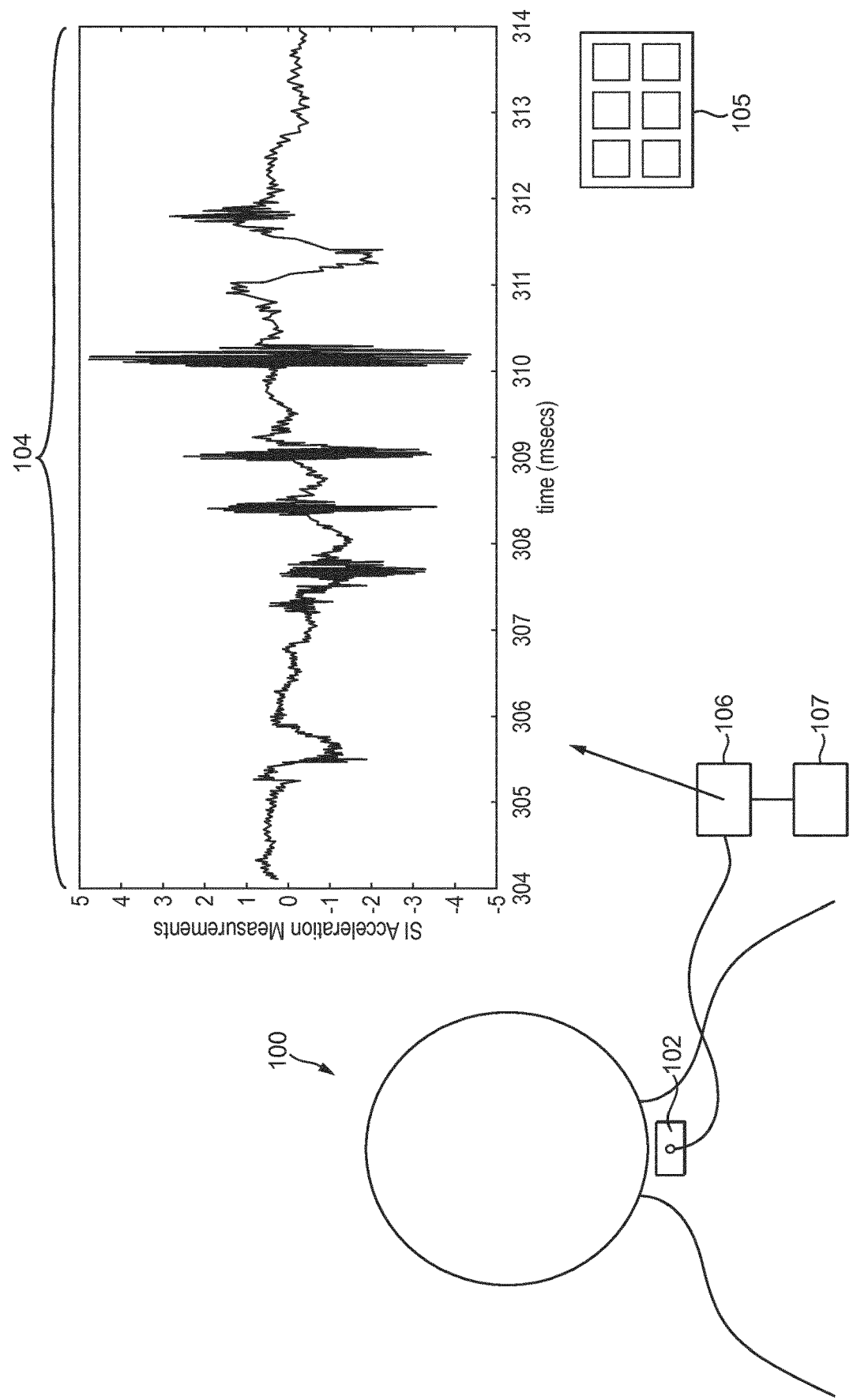
FIG. 2 is a schematic diagram of an embodiment of a device for screening swallowing impairment during operation.

FIG. 2 generally illustrates a non-limiting example of a device 100 for screening swallowing safety and swallowing efficiency. The device 100 can comprise a sensor 102 (e.g., a dual axis accelerometer) to be attached in a throat area of a candidate for acquiring dual axis accelerometry data and/or signals during swallowing, for example illustrative S-I acceleration signal on a user interface 104. Accelerometry data may include, but is not limited to, throat vibration signals acquired along the anterior-posterior axis (A-P) and/or the superior-inferior axis (S-I). The sensor 102 can be any accelerometer known to one of skill in this art, for example a single axis accelerometer (which can be rotated on the patient to obtain dual-axis vibrational data) such as an EMT 25-C single axis accelerometer or a dual axis accelerometer such as an ADXL322 or ADXL327 dual axis accelerometer, and the present disclosure is not limited to a specific embodiment of the sensor 102.

The sensor 102 can be operatively coupled to a processor 106 configured to process the acquired data for swallowing impairment detection, for example aspiration-penetration detection and/or detection of other swallowing impairments such as swallowing inefficiencies. The processor 106 can be a distinctly implemented device operatively coupled to the sensor 102 for communication of data thereto, for example, by one or more data communication media such as wires, cables, optical fibers, and the like and/or by one or more wireless data transfer protocols. In some embodiments, the processor 106 may be implemented integrally with the sensor 102.

Generally, the processing of the dual-axis accelerometry signals comprises at least one of (i) a process in which at least a portion of the A-P signal and at least a portion of the S-I signal are analyzed individually by calculating the meta-features of each signal separately from the other channel or (ii) a process combining at least a portion of the axis-specific vibrational data for the A-P axis with at least a portion of the axis-specific vibrational data for the S-I axis and then extracting meta-features from the combined data. Then the swallowing event can be classified based on the extracted meta-features. In applying this approach, the swallowing events may be effectively classified as a normal swallowing event or a potentially impaired swallowing events (e.g., unsafe and/or inefficient). Preferably the classification is automatic such that no user input is needed for the dual-axis accelerometry signals to be processed and used for classification of the swallow.

In a preferred embodiment, the processor 106 of the device 100 is configured to receive first accelerometry data for a first plurality of swallowing events executed successively by a first individual. The sensor 102 of the device 100 can be an accelerometer communicatively connected to the processor 102 to provide the first accelerometry data.

The processor 106 can compare swallowing data (e.g., at least a portion of the first accelerometry data and/or at least a portion of second accelerometry data derived from the first accelerometry data) against preset classification criteria defined for each of swallowing safety and swallowing efficiency.

In a preferred embodiment, a bolus can be administered to an individual for screening swallowing impairment, and the processor 106 can subject the accelerometry data corresponding to the bolus (e.g., at least a portion of the first accelerometry data and/or at least a portion of second accelerometry data derived from the first accelerometry data) to one more of the following four grey methods to detect if the signal quality is valid for a classification model. Preferably at least two of the grey methods are implemented, more preferably at least three, most preferably all four. If the one or more grey methods applied to the accelerometry data corresponding to the bolus detect insufficient signal quality of the accelerometry data, the acclerometry data and/or the bolus can be identified, preferably by at least one of audio or graphics provided by the device 100, and preferably analysis of the accelerometry data corresponding to the bolus is discontinued by the processor 106.

A first grey method can identify if the accelerometry data corresponding to the bolus represents a missing swallow. The first grey method can comprise determining, on the processor 106, the signal variance of the accelerometry data in function of time, as a summed power over a specific frequency range of a summed spectrogram sp between S-I and A-P signals, preferably in a frequency range (e.g., the frequency range below 1.25 kHz), and can be compared to an upper threshold value to detect a missing swallow. As a non-limiting example, the upper threshold value for a missing swallow can be 75.

A second grey method can identify if the accelerometry data corresponding to the bolus was clipped from the start. The second grey method can comprise the processor 106 determining the normalized variance signal varDB from an A-P and S-I signal summed spectrogram, and a beginning portion of the normalized variance signal can be selected. As a non-limiting example, the beginning portion of the normalized variance signal can be the first 0.16 seconds of the normalized variance signal. If the beginning portion of the normalized variance signal includes any value equal or higher than a threshold value (e.g., a value that is 95% of the maximum), the dual-axis accelerometry data can be identified as "clipped from start."

A third grey method can identify if the accelerometry data corresponding to the bolus was clipped from the end. The third grey method can comprise determining, on the processor 106, the normalized variance signal varDB from an A-P and S-I signal summed spectrogram, and an end portion of the normalized variance signal can be selected. As a non-limiting example, the end portion of the normalized variance signal can be the last 0.16 seconds of the normalized variance signal. If the end portion of the variance signal includes any value equal or higher than a threshold value (e.g., a value that is maximum), the bolus corresponding to the dual-axis accelerometry data can be identified as "clipped from end."

A fourth grey method can perform noise detection. The fourth grey method can comprise the processor 106 applying spectral entropy for the summed power spectral density (PSD) of both S-I and A-P signals. The PSD can be determined as an average of the spectrogram over the whole bolus length, and the spectral entropy for the summed PSD can be determined for a frequency range (e.g., the frequency range below 1.25 kHz). The following non-limiting technique for the spectral entropy follows the original method of information theory, for computing Shannon entropy from the probability distribution function.

The total spectrogram can be computed by a dot sum of the signal channel Pxx matrixes:

Pxx_tot=Pxx_AP+Pxx_SI

The PSD can be computed as an average over the whole bolus time:

PSD=mean(Pxx_tot(over sp_t))

The PSD in frequency range can be selected:

PSDindf=PSD(select sp_f<1250 Hz)

The PSD can be normalized to show a probability distribution function over the selected frequency range:

PSDnorm=PSDindf/sum(PDFindf)

The spectral entropy Etot can be computed as sum of a dot product between normalized PSD and log 2( ) of it, and finally the negative sum is taken and divided by log 2( ) of the length of vector Edot (number of frequency bins below 1.25 kHz):

Edot=(SDnorm*log 2(PSDnorm);

Edot(PSDnorm==0)=0;

Etot=−sum(Edot)/log 2(length(Edot))

The Edot values can be set to zero for the indexes in which PSDnorm was zero, as log 2(0) would be negative infinitive. The operations can scale the spectral entropy Etot to range between 0 and 1, the higher entropy values showing more information content, i.e., in this application, a more noisy signal.

In a preferred embodiment, the fourth grey method further comprises an additional detection for noise peak artefacts in the signal. Taken into account the averaging operations during the computation of the variance signal varBW, the resulted segmentation length has been noticed to be longer than 0.7 seconds for any swallowing movements, recorded by the dual-axis accelerometry. Therefore, if the segmentation period Dsegs2-Dsegs1 is shorter than a threshold (e.g., 0.5 seconds), the signal contains a very sharp peak artefact, and the dual-axis accelerometry data for the bolus can be identified as having noise.

If analysis of the accelerometry data continues after application of the one or more grey methods (e.g., the one or more grey methods confirm desired signal quality), the processor 106 can classify each of the first plurality of swallowing events with a swallowing safety classification and a swallowing efficiency classification based at least partially on the comparing of the swallowing data against the preset classification criteria. The swallowing safety classification is identified from at least two predetermined swallowing safety classifications, and the swallowing efficiency classification is identified from at least two predetermined swallowing efficiency classifications.

Each of the first plurality of swallowing events is classified independently from the other swallowing events to provide independent point measurements for the first plurality of swallowing events. Preferably, classification by the processor 106 of each of the first plurality of swallowing events is real-time relative to the corresponding swallowing event.

The user interface 104 of the device 100 is preferably configured to provide one or more first outputs comprising at least one of audio or graphics that identify the swallowing safety classification and the swallowing efficiency classification for each of the first plurality of swallowing events. Preferably, the one or more first outputs by the user interface 104 are each real-time relative to the corresponding swallowing event. The user interface 104 can comprise an input element 105 (e.g., a keyboard or touchpad) that is configured to accept user input identifying at least one parameter selected from the group consisting of a type of sensor that provides the first accelerometry data and a type of beverage consumed during the first plurality of swallowing events. In a preferred embodiment, the one or more first outputs can identify if the signal quality was insufficient for one or more of the first plurality of swallowing events.

In an embodiment, the device 100 further comprises a housing, and the processor 106 and the user interface 104 are positioned within the housing and/or mechanically connected to the housing.

The processor 106 can be configured to use the user interface 104 to identify the swallowing safety classification and the swallowing efficiency classification for the first swallowing event simultaneously relative to each other. In an embodiment, the processor 106 is configured to use the user interface 104 to provide one or more second user outputs comprising at least one of audio or graphics that instruct administration of a plurality of doses of beverage, and each of the first plurality of swallowing events correspond to one of the plurality of doses of beverage. For example, the processor 106 can be configured to use the user interface 104 to instruct administration of a first dose of beverage, then identify the swallowing safety classification and the swallowing efficiency classification for a first swallowing event corresponding to the first dose of beverage (or identify insufficient signal quality for the data from the first swallowing event), then instruct administration of a second dose of beverage, and then identify the swallowing safety classification and the swallowing efficiency classification for a second swallowing event corresponding to the second dose of beverage (or identify insufficient signal quality for the data from the second swallowing event).

The processor 106 can be configured to use the user interface 104, after identifying the swallowing safety classification and the swallowing efficiency classification for the second swallowing event, to instruct administration of a third dose of beverage, and then identify the swallowing safety classification and the swallowing efficiency classification for a third swallowing event corresponding to the third dose of beverage (or identify insufficient signal quality for the data from the third swallowing event). The processor 106 can be configured to use the user interface 104, after identifying the swallowing safety classification and the swallowing efficiency classification for the third swallowing event, to instruct administration of a fourth dose of beverage, and then identify the swallowing safety classification and the swallowing efficiency classification for a fourth swallowing event corresponding to the fourth dose of beverage (or identify insufficient signal quality for the data from the fourth swallowing event).

In an embodiment, the at least two predetermined swallowing safety classifications comprise a first swallowing safety classification indicative of a safe event and a second swallowing safety classification indicative of an unsafe event. The at least two predetermined swallowing efficiency classifications can comprise a first swallowing efficiency classification indicative of an efficient event and a second swallowing efficiency classification indicative of an inefficient event. The one or more first outputs can comprise at least one icon displayed on the user interface 104 for each of the first plurality of swallowing events, at least a portion of the at least one icon can be a first color for the first swallowing safety classification or a second color different than the first color for the second swallowing safety classification, and at least a portion of the at least one icon can be a third color for the first swallowing efficiency classification or a fourth color different than the third color for the second swallowing efficiency classification. Preferably the first and third colors are the same color, and the second and fourth colors are the same color.

In a preferred embodiment, at least a portion of the at least one icon can be a fifth color different than the first, second, third and fourth colors to identify insufficient signal quality for the data from the corresponding swallowing event. As a non-limiting example, the first and third colors can be green, the second and fourth colors can be red, and the fifth color can be grey.

In an embodiment, the device 100 comprises a memory element 107 configured to store the swallowing safety classification and the swallowing efficiency classification for each of the first plurality of swallowing events in a first profile associated with the first individual. The device 100 can be used to monitor the first individual by periodically screening the first individual and saving the results of the periodic screenings in the memory element 107.

In a preferred embodiment, the device 100 can screen the individual for swallowing safety and swallowing efficiency for each of a plurality of beverages, such as one or more of water (50 mPa·s or less, e.g. 1 mPa·s), nectar (51-350 mPa·s·, honey (351-1750 mPa·s) or pudding (>1750 mPa·s), and most preferably screen each type of beverage separately (i.e., first screen one or more boluses of a first beverage, then screen one or more boluses of a second beverage). The device 100 can screen the first individual for one or more types of beverages at a first time and then screen the individual for the one or more types of beverages again periodically thereafter, for example one week, one month, or one year between screenings.

For example, the processor 106 can be configured to screen a second plurality of swallowing events executed by the first individual subsequent to the first plurality of swallowing events, the first plurality of swallowing events executed on a first beverage having a first viscosity, and the second plurality of swallowing events executed on a second beverage having a second viscosity different than the first viscosity. The processor 106 can be configured to store (e.g., in the memory element 107) the swallowing safety classification and the swallowing efficiency classification for each of the first plurality of swallowing events in association with identification of the first beverage in the first profile associated with the first individual. The processor 106 can be configured to store (e.g., in the memory element 107) the swallowing safety classification and the swallowing efficiency classification for each of the second plurality of swallowing events in association with identification of the second beverage in the first profile associated with the first individual.

The device 100 can be used to screen and/or monitor a plurality of individuals, e.g., the first individual, a second individual and optionally additional individuals, preferably autonomously (i.e., the screening results are separate for each individual relative to the screening results of the other individuals). Each of the plurality of individuals can have their own profile and preferably can be screened the same day as the other individuals if desired.

For example, the processor 106 can be configured to compare the swallowing safety and efficiency classifications for the first plurality of swallowing events to the swallowing safety and efficiency classifications for the second plurality of swallowing events. The processor 106 can be configured to screen a second plurality of swallowing events executed by a second individual different than the first individual subsequent to the first plurality of swallowing events and store (e.g., in the memory element 107) the swallowing safety classification and the swallowing efficiency classification for each of the second plurality of swallowing events in a second profile associated with the second individual.

In an embodiment, the processor 106 is configured to screen a second plurality of swallowing events executed by the first individual subsequent to the first plurality of swallowing events, and the processor 106 is configured to compare the swallowing safety and efficiency classifications for the first plurality of swallowing events to the swallowing safety and efficiency classifications for the second plurality of swallowing events.

Figure 3:
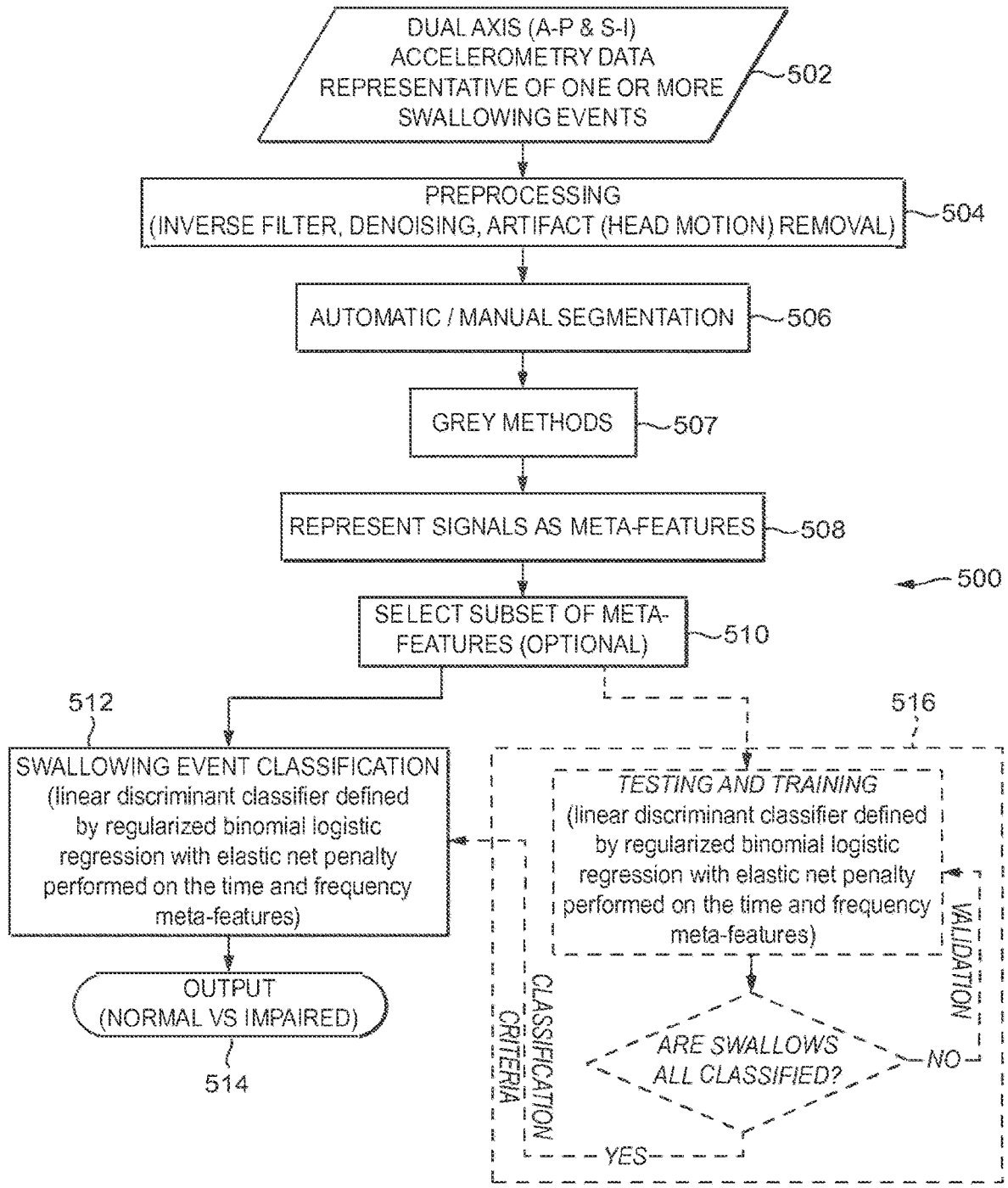
FIG. 3 is a schematic diagram of an embodiment of a method of screening swallowing impairment.

FIG. 3 illustrates a non-limiting embodiment of a method 500 for classifying a swallowing event. At Step 502, dual-axis accelerometry data for both the S-I axis and the A-P axis is acquired or provided for one or more swallowing events, for example dual-axis accelerometry data from the sensor 102.

At Step 504, the dual-axis accelerometry data can optionally be processed to condition the accelerometry data and thus facilitate further processing thereof. For example, the dual-axis accelerometry data may be filtered, denoised, and/or processed for signal artifact removal ("preprocessed data"). In an embodiment, the dual-axis accelerometry data is subjected to an inverse filter, which may include various low-pass, band-pass and/or high-pass filters, followed by signal amplification. A denoising subroutine can then applied to the inverse filtered data, preferably processing signal wavelets and iterating to find a minimum mean square error.

In an embodiment, the preprocessing may comprise a subroutine for the removal of movement artifacts from the data, for example, in relation to head movement by the patient. Additionally or alternatively, other signal artifacts, such as vocalization and blood flow, may be removed from the dual-axis accelerometry data. Nevertheless, the method 500 is not limited to a specific embodiment of the preprocessing of the accelerometry data, and the preprocessing may comprise any known method for filtering, denoising and/or removing signal artifacts.

At Step 506, the accelerometry data (either raw or preprocessed) can then be automatically or manually segmented into distinct swallowing events. Preferably the accelerometry data is automatically segmented. In an embodiment, the segmentation is automatic and energy-based. Additionally or alternatively, manual segmentation may be applied, for example by visual inspection of the data. The method 500 is not limited to a specific process of segmentation, and the process of segmentation can be any segmentation process known to one skilled in this art.

At Step 507, one or more of the grey methods detailed above are applied to the accelerometry data, preferably at least two of the grey methods, more preferably at least three of the grey methods, most preferably all four of the grey methods. The one or more grey methods are preferably performed after the signal segmentation of Step 506 because some of the intermediate variables computed in the signal segmentation block can also be applied for the one or more grey methods, although the detections from the one or more grey methods are preferably defined for the non-segmented whole signal length.

At Step 508, meta-feature based representation of the accelerometry data can be performed. For example, one or more time-frequency domain features can be calculated for each axis-specific data set. Combinations of extracted features may be considered herein without departing from the general scope and nature of the present disclosure. Preferably different features are extracted for each axis-specific data set, but in some embodiments the same features may be extracted in each case. Furthermore, other features may be considered for feature extraction, for example, including one or more time, frequency and/or time-frequency domain features (e.g., mean, variance, center frequency, etc.).

At Step 510 (which is optional), a subset of the meta-features may be selected for classification, for example based on the previous analysis of similar extracted feature sets derived during classifier training and/or calibration. For example, in one embodiment, the most prominent features or feature components/levels extracted from the classifier training data set are retained as most likely to provide classifiable results when applied to new test data, and are thus selected to define a reduced feature set for training the classifier and ultimately enabling classification. For instance, in the context of wavelet decompositions, or other such signal decompositions, techniques such as linear discriminant analysis, principle component analysis or other such techniques effectively implemented to qualify a quantity and/or quality of information available from a given decomposition level, may be used on the training data set to preselect feature components or levels most likely to provide the highest level of usable information in classifying newly acquired signals. Such preselected feature components/levels can then be used to train the classifier for subsequent classifications. Ultimately, these preselected features can be used in characterizing the classification criteria for subsequent classifications.

Accordingly, where the device has been configured to operate from a reduced feature set, such as described above, this reduced feature set can be characterized by a predefined feature subset or feature reduction criteria that resulted from the previous implementation of a feature reduction technique on the classifier training data set. Newly acquired data can thus proceed through the various pre-processing and segmentation steps described above (steps 504, 506), the various swallowing events so identified then processed for feature extraction at step 508 (e.g., full feature set), and those features corresponding with the preselected subset retained at step 510 for classification at step 512.

While the above exemplary approach contemplates a discrete selection of the most prominent features, other techniques may also readily apply. For example, in some embodiments, the results of the feature reduction process may rather be manifested in a weighted series or vector for association with the extracted feature set in assigning a particular weight or level of significance to each extracted feature component or level during the classification process. In particular, selection of the most prominent feature components to be used for classification can be implemented via linear discriminant analysis (LDA) on the classifier training data set. Consequently, feature extraction and reduction can be effectively used to distinguish safe swallows from potentially unsafe swallows, and efficient swallows from potentially inefficient swallows. In this regard, the extraction of the selected features from new test data can be compared to preset classification criteria established as a function of these same selected features as previously extracted and reduced from an adequate training data set, to classify the new test data as representative of a normal vs. impaired swallow (e.g., safe swallows vs. unsafe swallows, and/or efficient swallows vs. inefficient swallows). As will be appreciated by the skilled artisan, other feature sets such as frequency, time and/or time-frequency domain features may be used.

At Step 512, feature classification can be implemented. Extracted features (or a reduced/weighted subset thereof) of acquired swallow-specific data can be compared with preset classification criteria to classify each data set as representative of a normal swallowing event or a potentially impaired swallowing event. FIG. 3 notes a non-limiting example of feature classification, namely using a linear discriminant classifier defined by regularized binomial logistic regression performed on the time and frequency meta-features. Nevertheless, the present disclosure is not limited to a specific embodiment of the feature classification, and the feature classification can be performed using any process known in the art, for example any of those disclosed in U.S. Pat. Nos. 7,749,177; 8,267,875; and 9,138,171; and U.S. Patent App. Publ. No. 2014/0228714, each of which is incorporated herein by reference in its entirety.

In an embodiment, the method 500 can optionally comprise a training/validation subroutine Step 516 in which a data set representative of multiple swallows is processed such that each swallow-specific data set ultimately experiences the preprocessing, feature extraction and feature reduction disclosed herein. A validation loop can be applied to the discriminant analysis-based classifier using a cross-validation test. After all events have been classified and validated, output criteria may be generated for future classification without necessarily applying further validation to the classification criteria. Alternatively, routine validation may be implemented to either refine the statistical significance of classification criteria, or again as a measure to accommodate specific equipment and/or protocol changes (e.g. recalibration of specific equipment, for example, upon replacing the accelerometer with same or different accelerometer type/model, changing operating conditions, new processing modules such as further preprocessing subroutines, artifact removal, additional feature extraction/reduction, etc.).

The classification can be used to determine and output which swallowing event represented a normal swallowing event as compared to a penetration, an aspiration, a swallowing safety impairment and/or an swallowing efficiency impairment at Step 514. In some embodiments, the swallowing event can be further classified as a safe event or an unsafe event.

For example, the user interface 104 of the device 100 can comprise a display that identifies a swallow or an aspiration using images such as text, icons, colors, lights turned on and off, and the like. Alternatively or additionally, the user interface 104 can comprise a speaker that identifies a swallow or an aspiration using auditory signals. The present disclosure is not limited to a specific embodiment of the output, and the output can be any means by which the user interface 104 identifies the classification of the swallowing event to a user of the device 100, such as a clinician or a patient.

The output may then be utilized in screening the tested candidate and provided to a clinician who can determine, for example, appropriate treatment, further testing, and/or proposed dietary or other related restrictions. For example, a clinician can adjust feedings by changing consistency or type of food and/or the size and/or frequency of mouthfuls offered to the patient. In this regard, a clinician can determine an acceptable beverage type for the individual if a particular beverage type provided better swallowing safety and/or better swallowing efficiency relative to other beverage types (e.g., an acceptable beverage type can be one or more of water, nectar, honey, or pudding).

Alternative types of vibration sensors other than accelerometers can be used with appropriate modifications to be the sensor 102. For example, a sensor can measure displacement (e.g, a microphone), while the processor 106 records displacement signals over time. As another example, a sensor can measure velocity, while the processor 106 records velocity signals over time. Such signals can then be converted into acceleration signals and processed as disclosed herein and/or by other techniques of feature extraction and classification appropriate for the type of received signal.

In a preferred embodiment, the method 500 comprises receiving, on the device 100 comprising the processor 106, first accelerometry data for a first plurality of swallowing events executed successively by a first individual. The method can comprise transmitting the first accelerometry data to the device 100 from the sensor 102 (e.g., an accelerometer communicatively connected to the device 100).

In a preferred embodiment, the method 500 comprises comparing, on the device 100, swallowing data (e.g., at least a portion of the first accelerometry data and/or at least a portion of second accelerometry data derived from the first accelerometry data) against preset classification criteria defined for each of swallowing safety and swallowing efficiency. The method 500 can comprise classifying each of the first plurality of swallowing events with a swallowing safety classification and a swallowing efficiency classification based at least partially on the comparing of the swallowing data against the preset classification criteria, the swallowing safety classification is identified from at least two predetermined swallowing safety classifications, and the swallowing efficiency classification is identified from at least two predetermined swallowing efficiency classifications.

Preferably, the device 100 classifies each of the first plurality of swallowing events independently from the other swallowing events to provide independent point measurements for the first plurality of swallowing events. The classifying by the device 100 of each of the first plurality of swallowing events can be real-time relative to the corresponding swallowing event.

In a preferred embodiment, the method 500 comprises producing, from the device 100 (e.g., from the user interface 104), one or more first outputs comprising at least one of audio or graphics that identify the swallowing safety classification and the swallowing efficiency classification for each of the first plurality of swallowing events. The one or more first outputs identifying of the swallowing safety classification and the swallowing efficiency classification for each of the first plurality of swallowing events can be real-time relative to the corresponding swallowing event.

In an embodiment, the device comprises a housing, and the processor 106 and the user interface 104 each are positioned within the housing and/or mechanically connected to the housing.

The method 500 can comprise accepting user input on the device 100 (e.g., on the user interface 104) user input identifying at least one parameter selected from the group consisting of a type of sensor that provides the first accelerometry data and a type of beverage consumed during the first plurality of swallowing events.

In an embodiment, the method 500 comprises producing, from the device 100, one or more second outputs comprising at least one of audio or graphics that instruct administration of a plurality of doses of beverage, and the first plurality of swallowing events each correspond to one of the plurality of doses of beverage. For example, the method 500 can comprise instructing administration of a first dose of beverage, then identifying the swallowing safety classification and the swallowing efficiency classification for a first swallowing event corresponding to the first dose of beverage, then instructing administration of a second dose of beverage, and then identifying the swallowing safety classification and the swallowing efficiency classification for a second swallowing event corresponding to the second dose of beverage. The device 100 (e.g., the user interface 104) can identify the swallowing safety classification and the swallowing efficiency classification for the first swallowing event simultaneously relative to each other. The method 500 can comprise, after the identifying of the swallowing safety classification and the swallowing efficiency classification for the second swallowing event, instructing administration of a third dose of beverage, then identifying the swallowing safety classification and the swallowing efficiency classification for a third swallowing event corresponding to the third dose of beverage. The method 500 can comprise, after the identifying of the swallowing safety classification and the swallowing efficiency classification for the third swallowing event, instructing administration of a fourth dose of beverage, then identifying the swallowing safety classification and the swallowing efficiency classification for a fourth swallowing event corresponding to the third dose of beverage.

In an embodiment, the at least two predetermined swallowing safety classifications comprise a first swallowing safety classification indicative of a safe event and a second swallowing safety classification indicative of an unsafe event, and the at least two predetermined swallowing efficiency classifications comprise a first swallowing efficiency classification indicative of an efficient event and a second swallowing efficiency classification indicative of an inefficient event. The one or more first outputs can comprise at least one icon for each of the first plurality of swallowing events, the at least one icon is displayed on the user interface 104 of the device 100, at least a portion of the at least one icon can be a first color for the first swallowing safety classification or a second color different than the first color for the second swallowing safety classification, and at least a portion of the at least one icon can be a third color for the first swallowing efficiency classification or a fourth color different than the third color for the second swallowing efficiency classification.

In an embodiment, the method 500 comprises storing the swallowing safety classification and the swallowing efficiency classification for each of the first plurality of swallowing events in the device 100 in a first profile associated with the first individual (e.g., in the storage element 107). The method 500 can further comprise: screening, with the device 100, a second plurality of swallowing events executed by the first individual subsequent to the first plurality of swallowing events, the first plurality of swallowing events executed on a first beverage having a first viscosity, and the second plurality of swallowing events executed on a second beverage having a second viscosity different than the first viscosity. Preferably, the method 500 comprises storing the swallowing safety classification and the swallowing efficiency classification for each of the first plurality of swallowing events on the device 100 (e.g., the storage element 107) in association with identification of the first beverage in the first profile associated with the first individual; and storing the swallowing safety classification and the swallowing efficiency classification for each of the second plurality of swallowing events on the device 100 (e.g., the storage element 107) in association with identification of the second beverage in the first profile associated with the first individual.

The method 500 can comprise comparing, on the device 100, the swallowing safety and efficiency classifications for the first plurality of swallowing events to the swallowing safety and efficiency classifications for the second plurality of swallowing events. The method 500 can comprise: screening, on the device 100, a second plurality of swallowing events executed by a second individual subsequent to the first plurality of swallowing events; and storing the swallowing safety classification and the swallowing efficiency classification for each of the second plurality of swallowing events in the device 100 in a second profile associated with the second individual (e.g., in the storage element 107).

In an embodiment, the method 500 comprises: screening, on the device 100, a second plurality of swallowing events executed by the first individual subsequent to the first plurality of swallowing events; and comparing, on the device 100, the swallowing safety and efficiency classifications for the first plurality of swallowing events to the swallowing safety and efficiency classifications for the second plurality of swallowing events.

EXAMPLE

The following clinical study presents scientific data developing and supporting one or more embodiments of a dysphagia screening device that uses parameters acquired from signal preprocessing and/or swallow segmentation of accelerometry data to identify an accelerometry signal as 1) a missing swallow, 2) clipped from start swallow, 3) clipped from end swallow or 4) noisy signal.

In this non-limiting example, the device read the accelerometry data from a sampling rate, e.g., a 10 kHz or 5 kHz sampling rate, and then downsampled the data, e.g., to a 2.5 kHz rate. The method for the downsampling included generating a spectrogram. The downsampling also included filtering out low-frequency head motion and mid-frequency swallow signal components of the signal and/or computation of one or more pre-processing related features.

The spectrogram was defined using parameters of window length and/or overlapping between the consequent windows in time. The main spectrogram result sp was applied for the swallow segmentation and thereafter for calculation of some of the features using the clipped sp of the segmented time indexes.

The parameters for computing the sp were as follows, assuming 2.5 kHz downsampled frequency:

sp.winlen=256; % [samples]

sp.fftlen=256; % [samples]

sp.ovpN=128; % window overlapping [samples]

sp.win=welch(sp.winlen); % window weighing function with Welch method (Welch: The Use of Fast Fourier Transform for the Estimation of Power Spectra: A Method Based on Time Averaging Over Short, Modified Periodograms IEEE Trans. Audio and Electroacoust., pp. 70-73, June 1967.)

A specific operation in the spectrogram routine was applied to remove fft-sidelobes effect of the DC-component within each window; assuming Xwin is signal over a specific window, for the first window segment this means:

sp.rmDC=true;

Xwin=signal(from 1 to sp.winlen);

XWdc=Xwin(:)'*sp.win(:)/sum(sp.win);

Xdc=mean(Xwin);

if (sp.rmDC)

Xwin=Xwin−Xdc;

Endif

The average Xdc used for the DC removal was computed without weighing with sp.win. However, a weighed average XWdc was also computed and applied for pre-processing.

The function call for spectrogramSonar( ) results into complex spectra, frequency and time axis, and Power spectral density (PSD):

[sp_AP,sp_f,sp_t,Pxx_AP,XWdc_AP]=spectrogram-
Sonar(APSignal,sp.win,sp.ovpN,sp.fftlen,FS,
sp.rmDC);

[sp_SI,~,~,Pxx_SI,XWdc_SI]=spectrogramSonar
(APsignal,sp.win,sp.ovpN,sp.fftlen,FS,sp.rmDC);

where:
sp_AP=complex spectra values for signal AP spectrogram
sp_f=frequency axis for the spectrogram from 0 Hz to FS/2 Hz
sp_t=time axis for the spectrogram (at each window mid point)
Pxx_AP=PSD values for signal AP spectrogram
XWdc_AP=vector of weighing averaged XWdc values for AP signal sampled at sp_t, and using weighing vector sp.win The total spectrogram was computed further by a dot sum of corresponding Pxx_matrixes: Pxx_tot=Pxx_AP+Pxx_SI;

The spectrogram frequency resolution was defined as: sp_df=sp_f[2]−sp_f[1];

Then signal segmentation was performed. The signal period including the swallow activity was estimated using the total spectrogram Pxx_tot and the corresponding frequency and time axis, as defined before.

Figure 4:
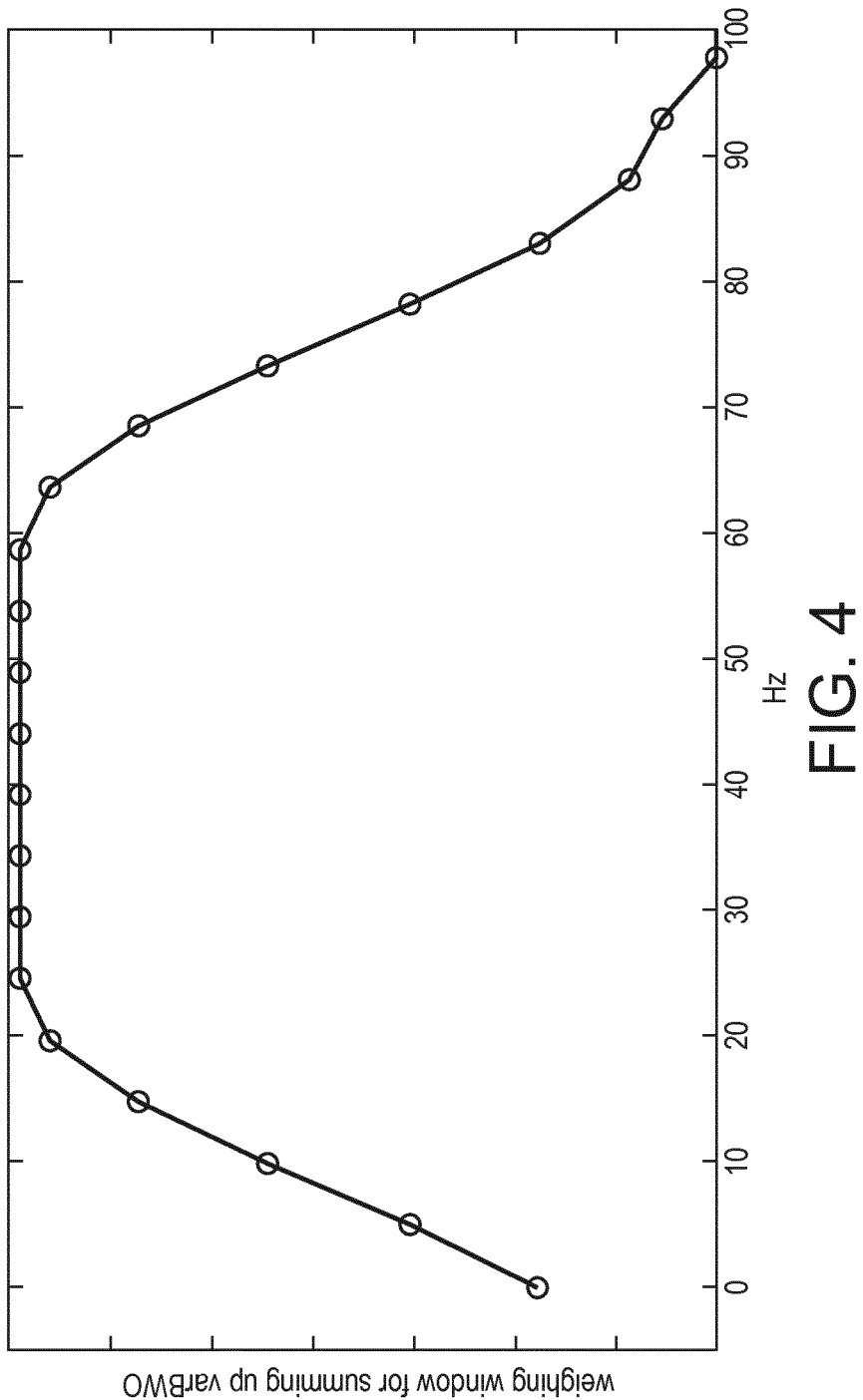
FIG. 4 is a graph of a weighing window for summing up Pxx_tot over frequency axis to result varBW0 in the non-limiting example of an embodiment of a device for screening swallowing impairment.

The segmentation was applied for the signal variance calculated from the Pxx_tot by summing up the PSD between frequencies 20 Hz and 60 Hz. However, the neighboring frequencies were also summed by weighing with Hamming window on both lower and higher frequency direction. The total length of underlying Hamming window function was seven samples in frequency axis, when using the sp.fftlen=256 and sampling rate of 2.5 kHz, and the resulted weighing function for summing up varBW0 was plotted in FIG. 4. The frequency resolution of this graph was twice better than with the final spectrogram parameters, and thus the length of the Hamming window was fifteen at the time, instead of the final seven.

The resulted variance signal was smoothed also along the spectrogram time axis with a Hamming window length of seven, in time axis samples to result into final varBW. The variance signal varBW was scaled to dB units, using −100 dB as the lower limit value, and normalized by setting the span between 0 and 1. The result was called varDB.

Figure 5:
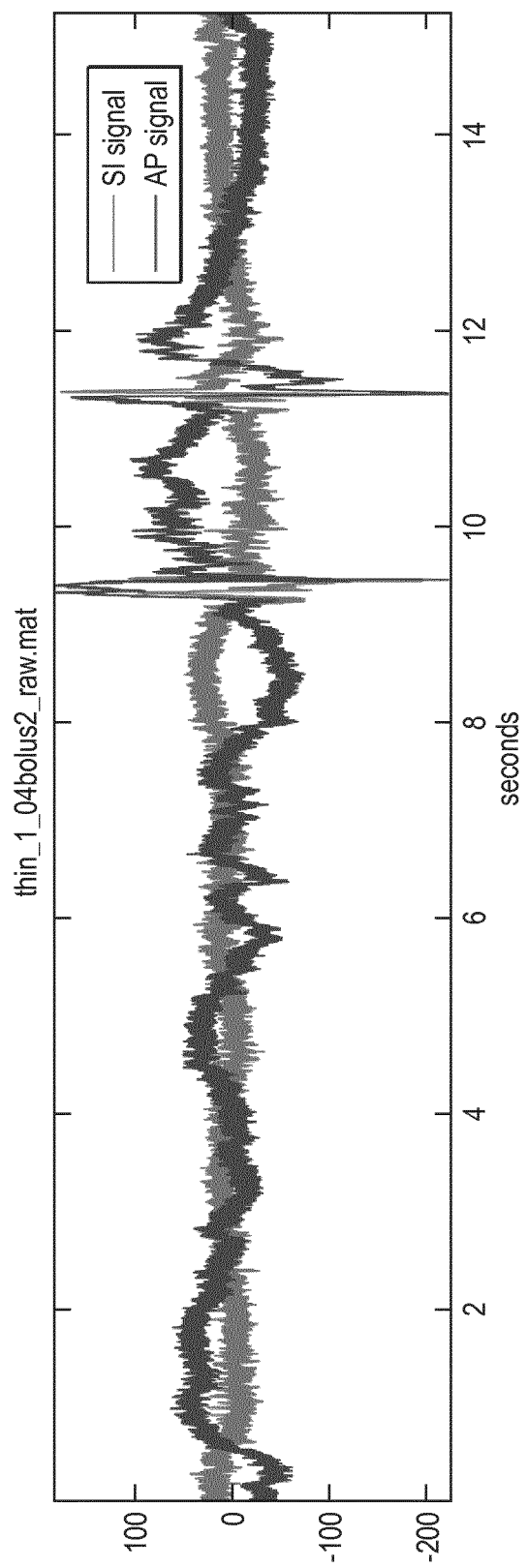
FIG. 5 contains graphs showing examples of both sensor signal and the variance signals; the segmentation times Dsegs1 and Dsegs2 for the analysis time span are shown in the lower graph.
Figure 5:
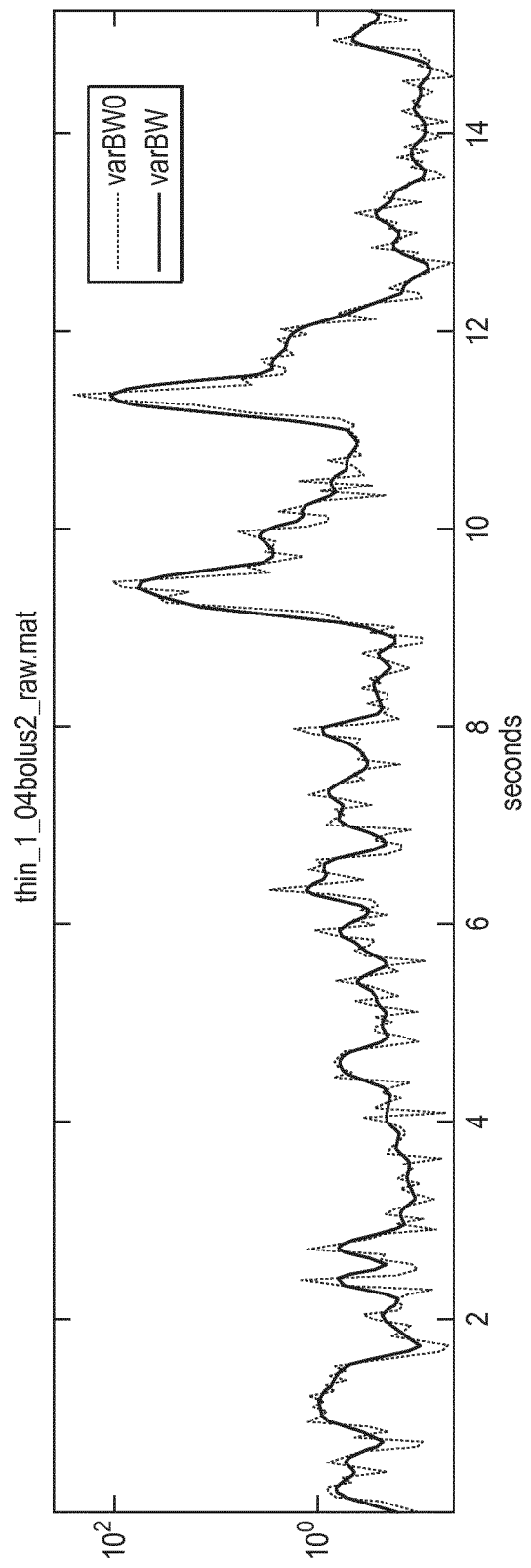
Figure 5:
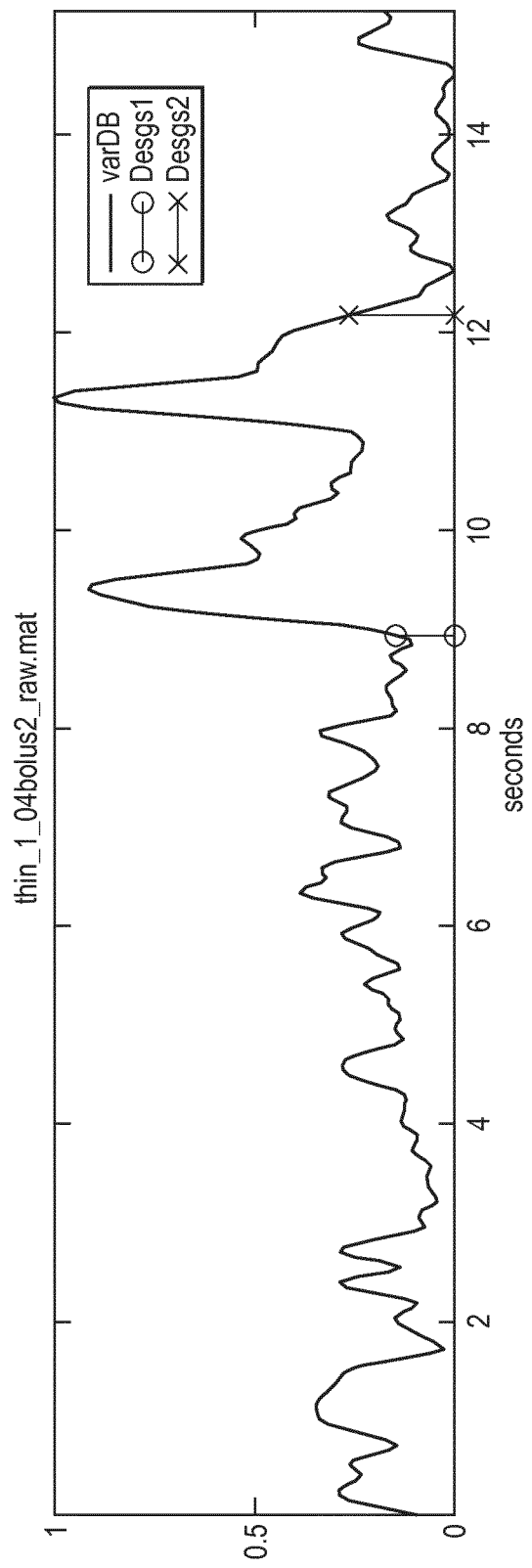

FIG. 5 shows an example for the variance signals varBW0, varBW and varDB. The vertical axis of the middle graph for varBW signals was scaled as logarithmic, and the lowest graph shows the dB scaled varDB with linear vertical axis. The normalized variance signal varDB was applied for segmentation by thresholding it. The segmentation firstly resulted into indexes related to spectrogram time axis, which finally have to be scaled for the original signal time axis.

First threshold parameter is Thres1, being 40% from the maximum of varDB, which was applied to find both the first segs_1, and the last segs_2 occurrence, exceeding Thres1.

Then, the second threshold parameter Thres2, being 15% from the maximum of varDB, was applied to extend the segs_1 into backwards direction to result for segs_3, and segs_2 into forwards direction to result for segs_4, by searching the first occurrence going under Thres2 value. If no values were found from varDB being less than Thres2, either from the start or end part of signal, the segs_3 was set for the first index of signal, or segs_4 was set for the last index of the signal, correspondingly.

Finally, the starting index Dsegs1 for the segment was selected as having the maximum second derivative between indexes segs_3 and segs_1. The final ending index Dsegs2 for the segment was selected as having the maximum second derivative between indexes segs_2 and segs_4. The second derivative was not computed for any of the start or end indexes segs_1 to segs_4, and thus the maximum was also not searched from those locations. If there were no indexes between segs_3 and segs_1, the Dsegs1 was set as the first one, i.e., segs_3. If there were no indexes between segs_2 and segs_4, the Dsegs2 was set as the first one, i.e., segs_2.

The second derivative above was computed in a central difference manner, taking the first derivative as forward difference and second derivative as backward difference from the first derivative.

For finalizing the segmentation, the segmentation time span between Dsegs1 for Dsegs2 was extended to be at least one second long, assuming that the signal time axis allows this. In case the found segment length was shorter than one second, it would be extended primarily for the signal end direction, i.e., up to APsignal.size( )/FS, but when necessary, it would be extended also for the starting direction, to result into total segment length of at least one second.

Finally, the segment indexes for the signals APsignal and SIsignal was defined by finding the corresponding time indices for the signal time axis, named as sigStart and sigEnd. Thereafter, the features were computed using the signal between these index values only. The same segment indexes were applied for the pre-processed signals Head_motion and Swallow_signal, for both AP and SI channels, as well.

In addition, the segmented spectrogram-based features used the spectrogram sp after segmentation, i.e., cropping of the time-axis sp_t including only the period between Dsegs1 for Dsegs2. Feature channel 35 was defined as the number of time samples of the segmented signal (i.e., the segmentation time span multiplied by sampling frequency).

Then the grey method detected if the signal quality was valid for the classification model. The grey detection fell into four classes: 1) missing swallow, 2) clipped from start swallow, 3) clipped from end swallow and 4) noisy signal, which are explained hereafter. With the phase0 data, the grey methods set about 3% of the boluses as grey, and as such, the sensor data safety or efficiency problem analysis is not continued.

Figure 6A:
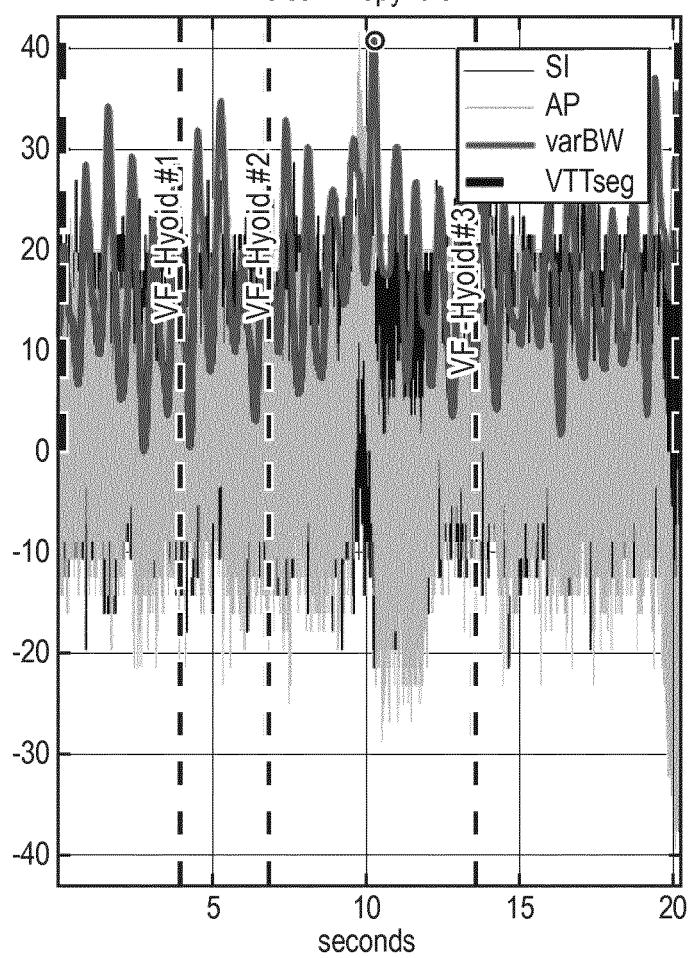
FIGS. 6A and 6B are graphs showing missing swallow examples for Phase0 thin and mild boluses.
Figure 6B:
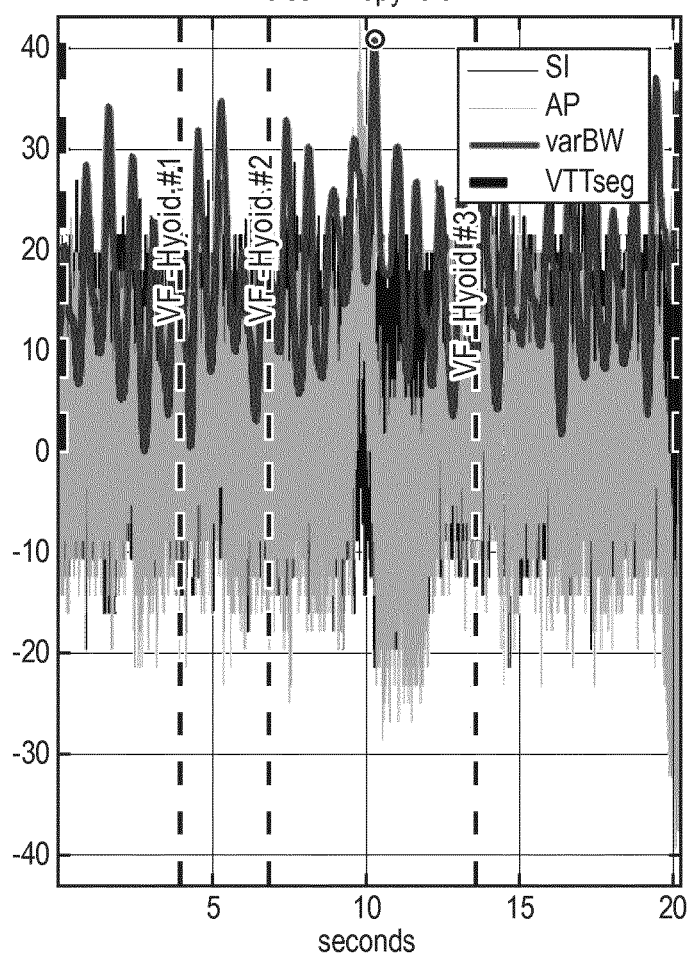

The missing swallow detection calculated the signal variance in function of time, as a summed power over a specific frequency range of the summed spectrogram sp between SI and AP signals, in the frequency range below 1.25 kHz, sp being defined previously. The upper threshold value for the missing swallow was 75. As shown in FIGS. 6A and 6B, the method resulted into one missing bolus over all boluses of the Phase0 thin (thin_SI_65 bolus1), and one missing bolus over all boluses of the Phase0 mild (mild_SI_65 bolus2). The second smallest variance found for all the thin boluses was about 120, which is clearly higher than the threshold value 75.

In the graph, S-I is red, A-P with blue, and summed variance signal is green. The normalized variance signal in the graph, varDB defined above, is not in scale and is also not directly showing total variance applied for missing swallow detection in here. The graphs were also computed for the data using the original sampling rate, and downsampling to 2.5 kHz may have changed the details somewhat.

Figure 7:
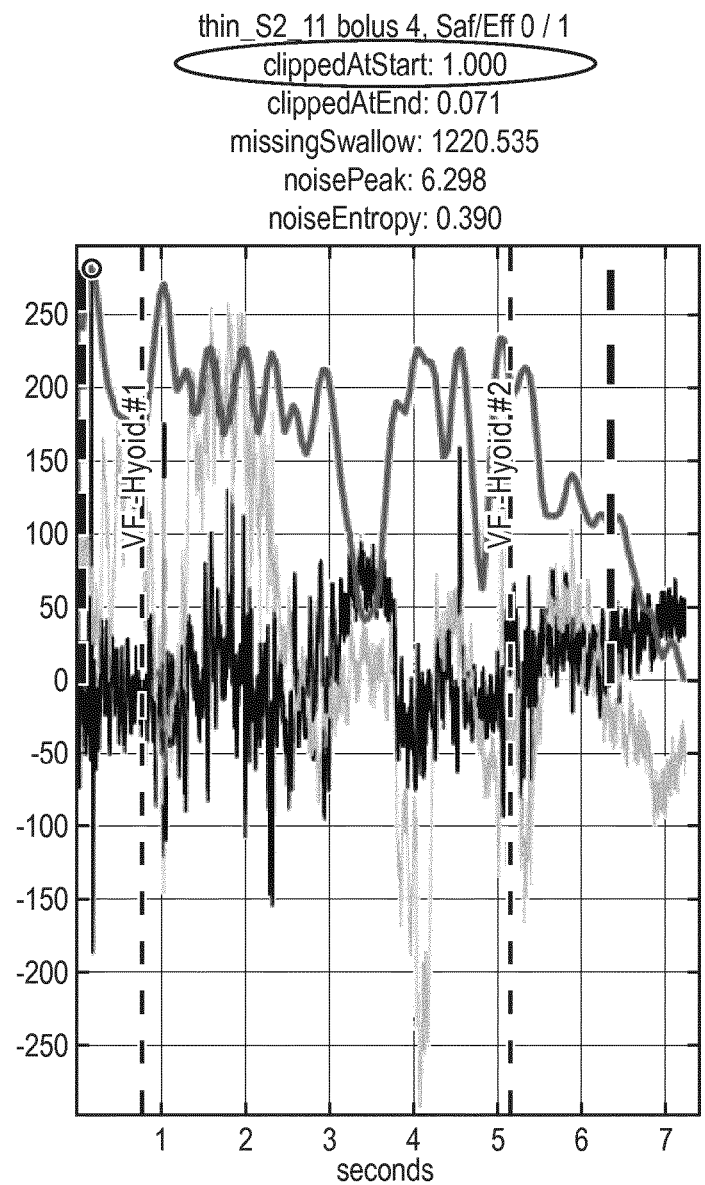
FIG. 7 contains graphs showing clipped from start example cases for Phase0 thin.
Figure 7:
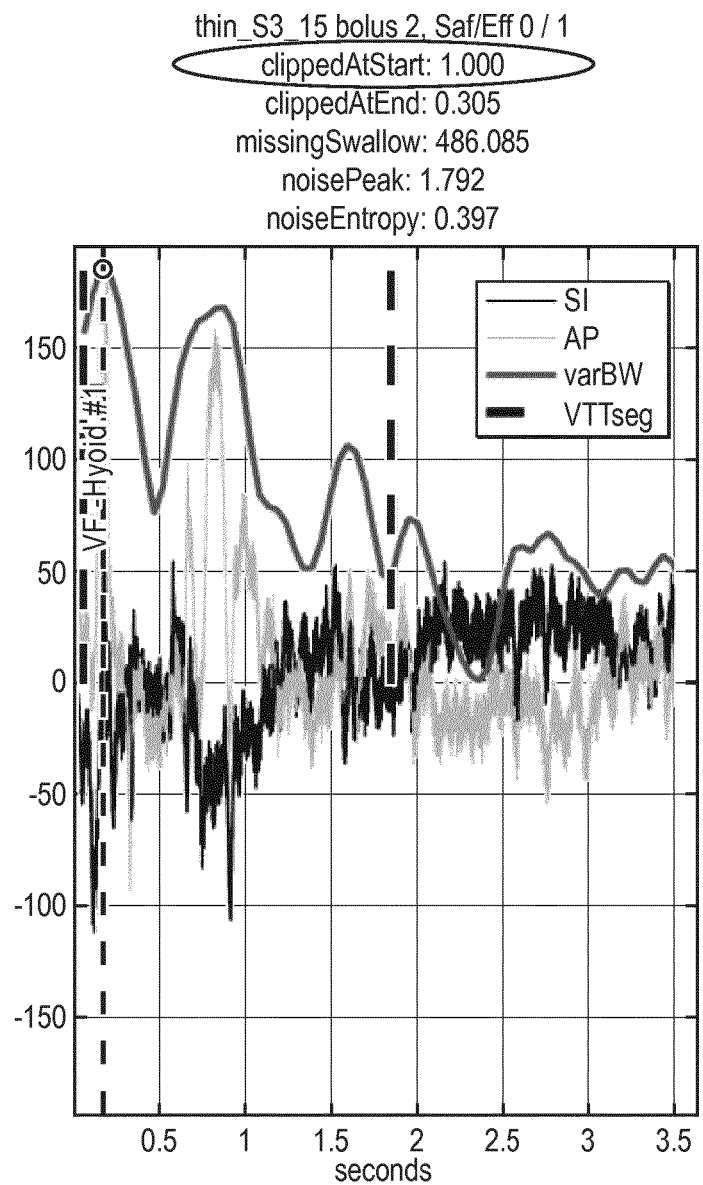
Figure 7:
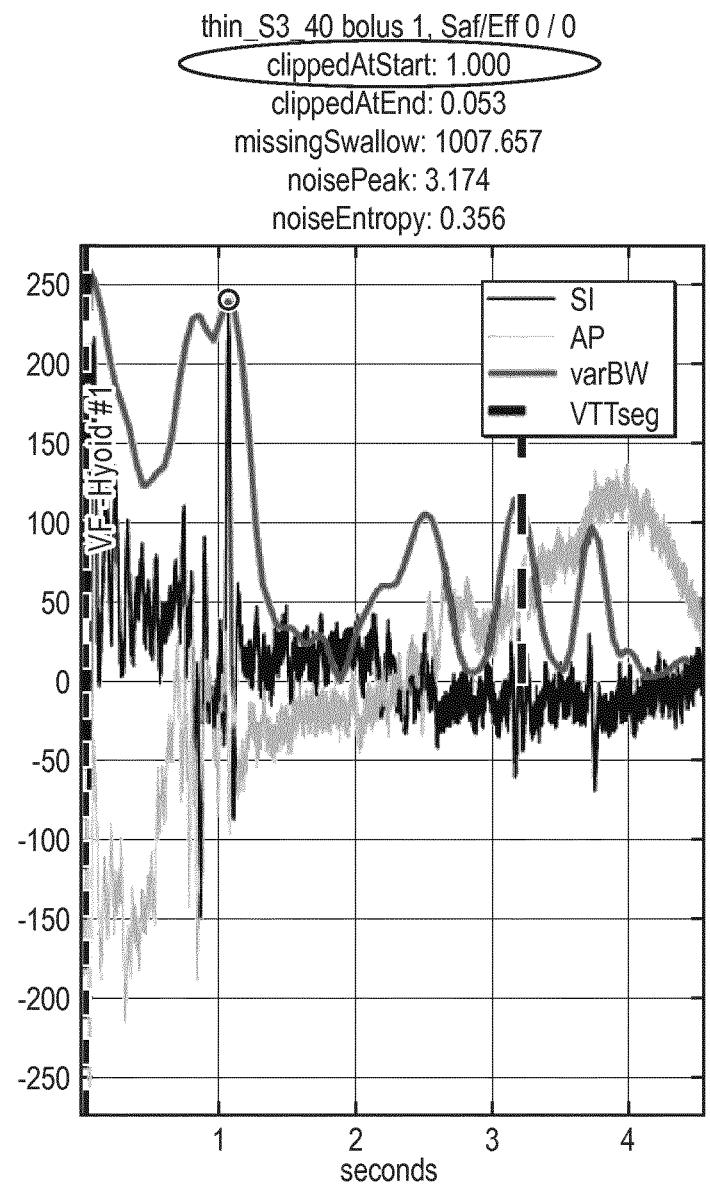

The clipped from start detection was based on the normalized variance signal varDB. The period before 0.16 seconds of the normalized variance signal was selected, and if it included any value higher than equal of the threshold value 95% from the maximum, the bolus was set as grey. FIG. 7 shows some examples of the headclipped signals. The vertical dashed line with cyan color shows that the reference swallow time code from the VF-analysis (hyoid burst start) were also indicating that the bolus recording started very late in correspondence with the swallowing start. Most probably, the late start of the VF-recording is not a problem for a reliable VF-analysis, but for the sensor algorithm it is important that the sensor signal recording is started in time.

Figure 8:
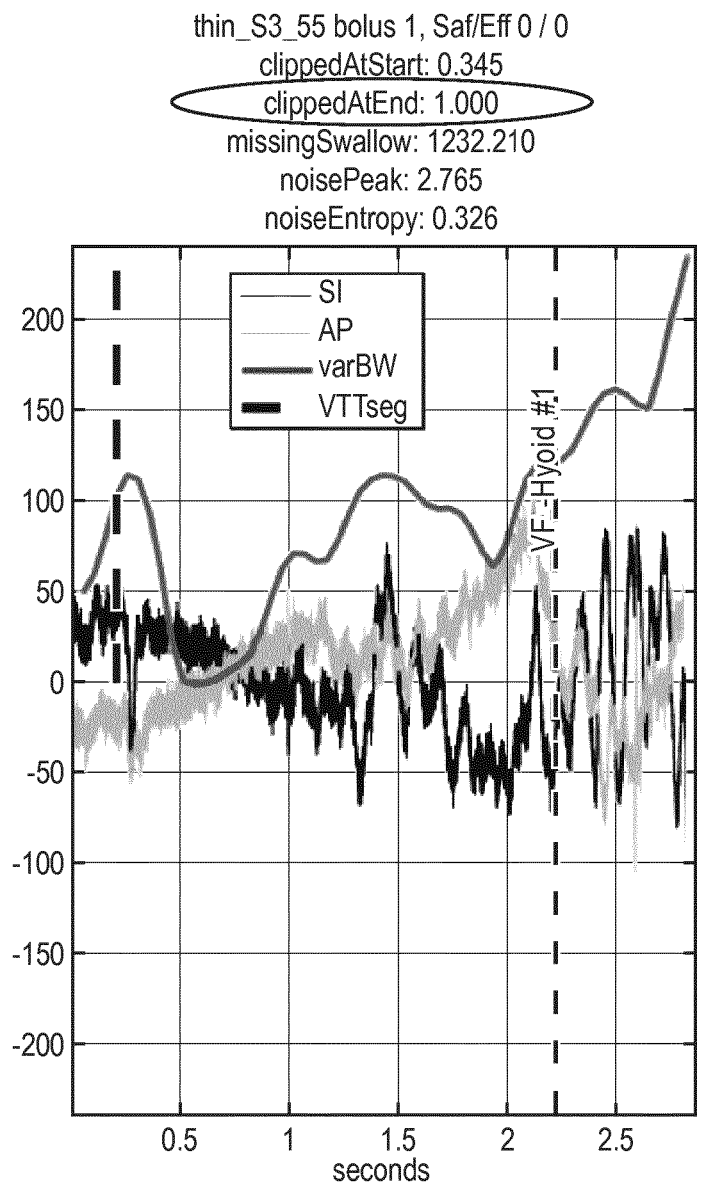
FIG. 8 contains graphs showing clipped from end example cases for Phase0 thin.
Figure 8:
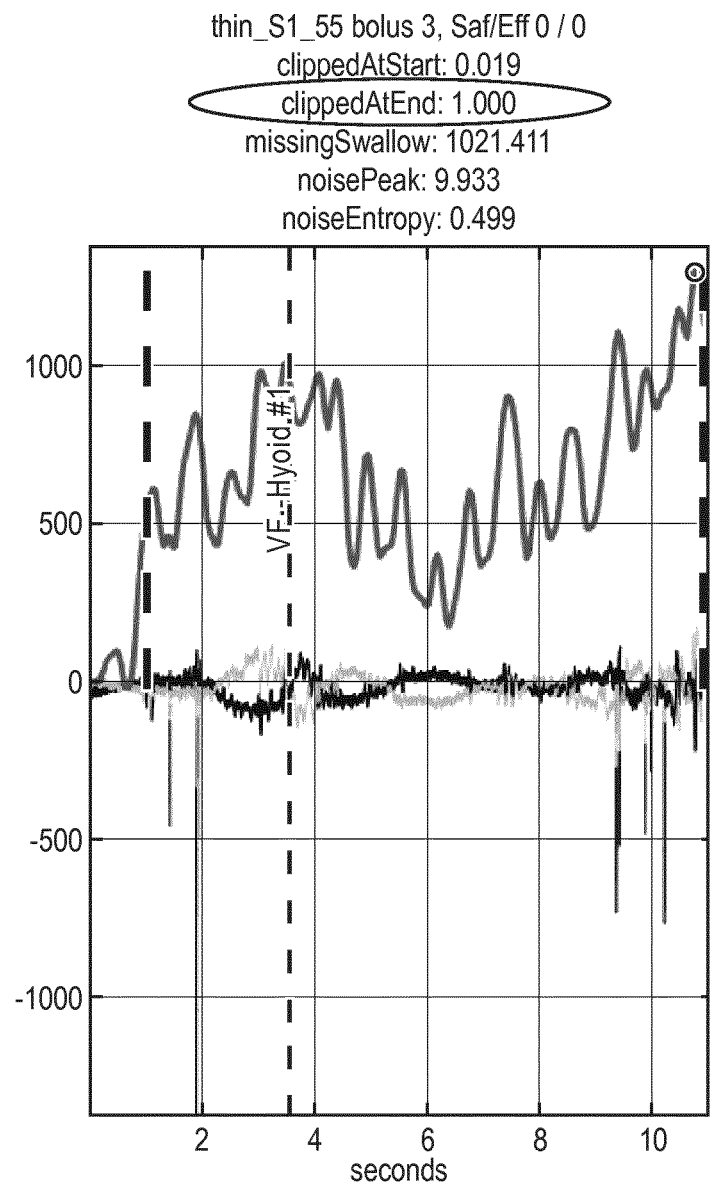
Figure 8:
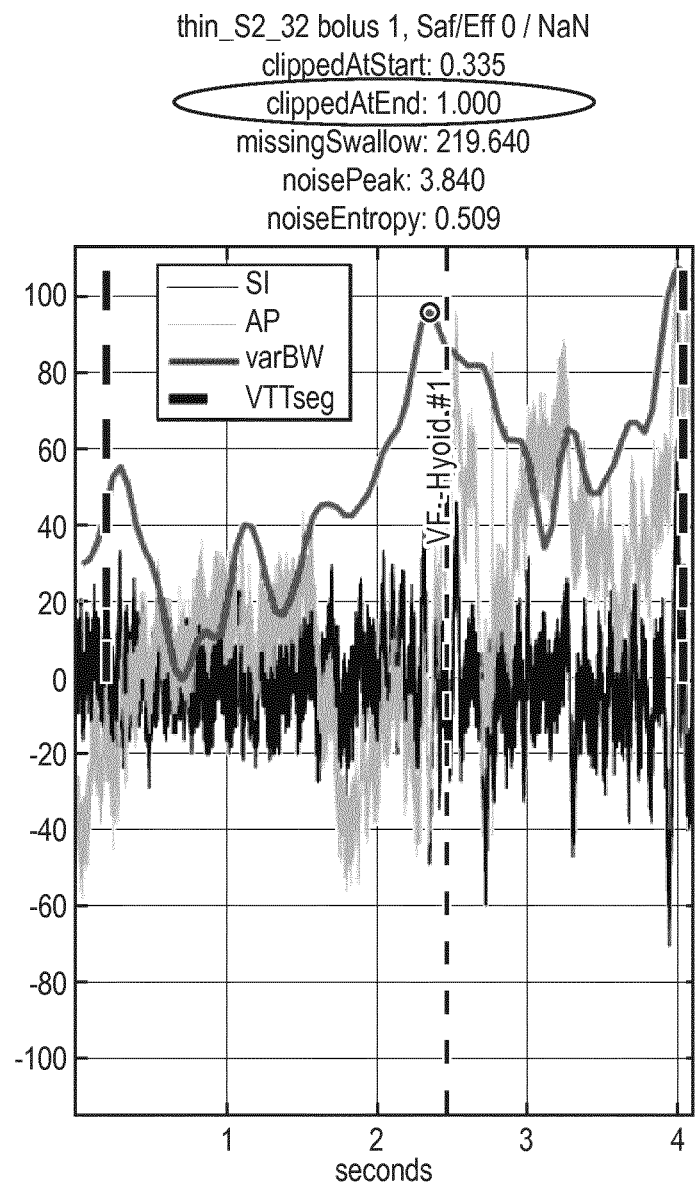

The clipped from end detection was based on the normalized variance signal varDB defined above. The period since 0.16 seconds before the bolus end time of the normalized variance signal was selected, and if it included any value equal with the maximum, the bolus was set as grey with a tailclip. FIG. 8 shows examples for the tailclip boluses.

The noise detection was based on spectral entropy, which was applied for the summed PSD (power spectral density) of both SI and AP signals. The PSD was computed as an average of the spectrogram over the whole bolus length, the spectrogram sp being defined previously herein. The spectral entropy for the summed PSD was then computed for the frequency range below 1.25 kHz:

The method below for the spectral entropy follows the original method of information theory, for computing Shannon entropy from the probability distribution function.

The total spectrogram was computed by a dot sum of the signal channel Pxx_matrixes:

$$Pxx\_tot=Pxx\_AP+Pxx\_SI;$$

The PSD was computed as an average over the whole bolus time:

$$PSD=mean(Pxx\_tot(over\ sp\_t));$$

The PSD in frequency range was selected:

$$PSDindf=PSD(select\ sp\_f<1250\ Hz);$$

Normalize PSD to show a probability distribution function over the selected frequency range $$PSDnorm=PSDindf/sum(PDFindf);$$

The spectral entropy Etot was computed as sum of a dot product between normalized PSD and log 2( ) of it, and finally the negative sum was taken and divided by log 2( ) of the length of vector Edot (number of frequency bins below 1.25 kHz):

$$Edot=PSDnorm.*log\ 2(PSDnorm);$$

$$Edot(PSDnorm==0)=0;$$

$$Etot=-sum(Edot)/log\ 2(length(Edot));$$

The Edot values were set to be 0 for the indexes in which PSDnorm was 0, as log 2(0) would be negative infinitive. The operations scaled the spectral entropy Etot to range between 0 and 1, the higher entropy values showing more information content, i.e., more noisy signal.

Figure 9A:
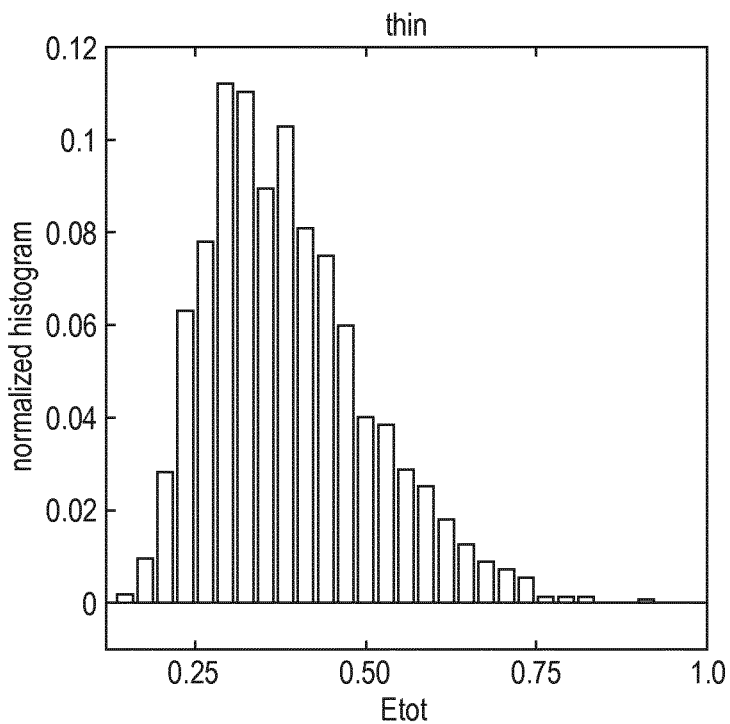
FIGS. 9A and 9B are histograms of spectral entropy for thin and mild boluses of Phase0 data.
Figure 9B:
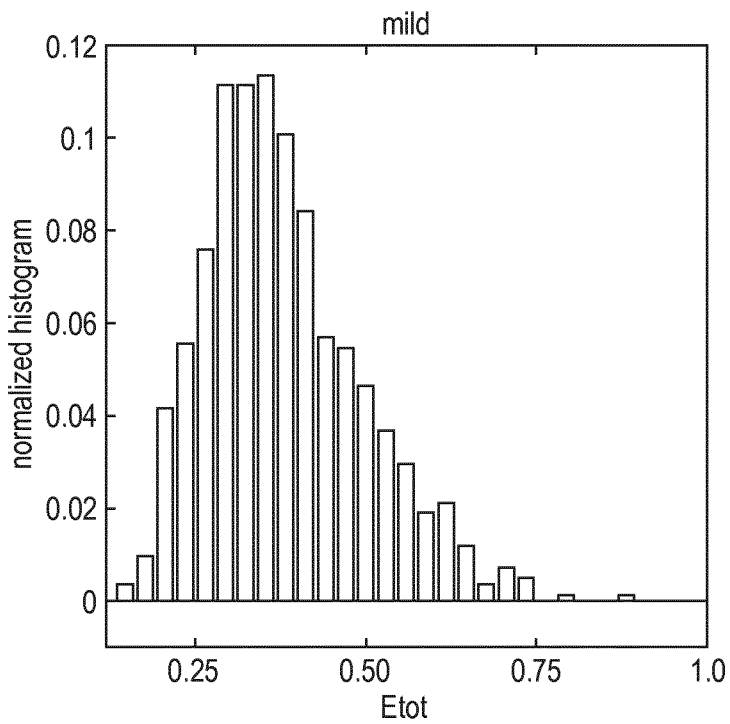

FIGS. 9A and 9B show the distribution of Etot for both thin and mild boluses of the Phase0 data. With the grey threshold for Etot>0.85, the noise detection resulted in total into three cases for the thin boluses and one case for mild. There was one bolus with highest entropy value, above 0.9, which was related for the missing swallow boluses shown already. This was expected; there was no patient movement during the bolus period, so the signal included mainly noise.

Figure 10:
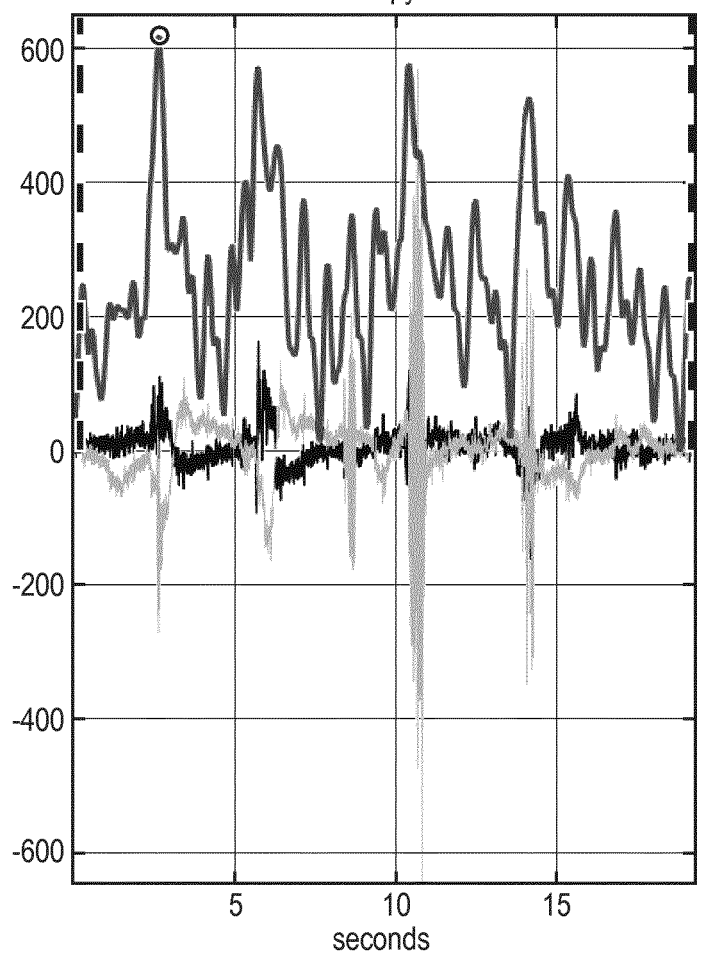
FIG. 10 is a graph showing an example for Phase0 thin giving noiseEntropy slightly less than the limit 0.85.

FIG. 10 shows an example for a bolus having sufficiently high noiseEntropy value, but not yet exceeding the threshold.

There was also an additional detection for noise peak artefacts in the signal. Taken into account the averaging operations during the computation of the variance signal varBW from segmentation, the resulted segmentation length was noticed to be longer than 0.7 seconds for any swallowing movements, recorded by the sensor during Phase0 pilots. Therefore, if the segmentation period Dsegs2-Dsegs1 ended up being shorter than the threshold 0.5 seconds, the signal contains a very sharp peak artefact, and the grey noise flag was given.

Various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A device for screening swallowing safety and swallowing efficiency, the device comprising:
a processor configured to receive accelerometry data of throat vibrations, determine vibration signals of the accelerometry data along an anterior-posterior axis and a superior-inferior axis of the throat to be used in determining a spectrogram, and perform at least one method comprising (i) determining a signal variance of the accelerometry data as a function of time, as summed power over a specific frequency range of the spectrogram, and comparing the signal variance to a first threshold value,
the at least one method further comprising at least one additional method selected from the group consisting of (ii) determining a normalized variance signal from the spectrogram by setting a span between 0 and 1, selecting a beginning portion of the normalized variance signal, and comparing values of the beginning portion of the normalized variance signal to a second threshold value, (iii) determining a normalized variance signal from the spectrogram by setting a span between 0 and 1, selecting an end portion of the normalized variance signal, and comparing values of the end portion of the normalized variance signal to a third threshold value, and (iv) determining a summed power spectral density of both the vibration signals along the anterior-posterior axis and the superior-inferior axis of the throat as an average of the spectrogram over a full duration or signal length relating to consumption of a single bolus and applying spectral entropy for the summed power spectral density (PSD) of the vibration signals along both the anterior-posterior axis and the superior-inferior axis of the throat for comparison to a fourth threshold value, wherein the at least one method is performed by the processor in real-time relative to receipt of the accelerometry data; and
a user interface configured to provide one or more outputs comprising at least one of audio or graphics, and the one or more outputs indicate a missing swallow for the accelerometry data based on one or more results of the at least one method.

2. The device of claim 1 further comprising an accelerometer communicatively connected to the processor to provide the accelerometry data.

3. A device for screening swallowing safety and swallowing efficiency, the device comprising:
a processor configured to receive accelerometry data of throat vibrations, determine vibration signals of the accelerometry data along an anterior-posterior axis and a superior-inferior axis of the throat to be used in determining a spectrogram, and perform at least one method comprising (i) determining a signal variance of the accelerometry data as a function of time, as summed power over a specific frequency range of the spectrogram, and comparing the signal variance to a first threshold value, and (ii) determining a normalized variance signal from the spectrogram by setting a span between 0 and 1, selecting a beginning portion of the normalized variance signal, and comparing values of the beginning portion of the normalized variance signal to a second threshold value,
the at least one method further comprising at least one additional method selected from the group consisting of (iii) determining a normalized variance signal from the spectrogram by setting a span between 0 and 1, selecting an end portion of the normalized variance signal, and comparing values of the end portion of the normalized variance signal to a third threshold value, and (iv) determining a summed power spectral density of both the vibration signals along the anterior-posterior axis and the superior-inferior axis of the throat as an average of the spectrogram over a full duration or signal length relating to consumption of a single bolus and applying spectral entropy for the summed power spectral density (PSD) of both vibration signals along the anterior-posterior axis and the superior-inferior axis of the throat for comparison to a fourth threshold value,
wherein the at least one method is performed by the processor in real-time relative to receipt of the accelerometry data; and
a user interface configured to provide one or more outputs comprising at least one of audio or graphics,
the one or more outputs indicate a missing swallow for the accelerometry data based on one or more results of the at least one method, and the one or more outputs indicate that the accelerometry data was clipped from a start based on one or more results of the at least one method.

4. A device for screening swallowing safety and swallowing efficiency, the device comprising:
a processor configured to receive accelerometry data of throat vibrations, determine vibration signals of the accelerometry data along an anterior-posterior axis and a superior-inferior axis of the throat to be used in determining a spectrogram, and perform at least one method comprising (i) determining a signal variance of the accelerometry data as a function of time, as summed power over a specific frequency range of the spectrogram, and comparing the signal variance to a first threshold value,
the at least one method further comprising at least one additional method selected from the group consisting of (ii) determining a normalized variance signal from the spectrogram by setting a span between 0 and 1, selecting a beginning portion of the normalized variance signal, and comparing values of the beginning portion of the normalized variance signal to a second threshold value, and (iv) determining a summed power spectral density of both the vibration signals along the anterior-posterior axis and the superior-inferior axis of the throat as an average of the spectrogram over a full duration or signal length relating to consumption of a single bolus and applying spectral entropy for the summed power spectral density (PSD) of both vibration signals along the anterior-posterior axis and the superior-inferior axis of the throat for comparison to a fourth threshold value,
the at least one method further comprising (iii) determining a normalized variance signal from the spectrogram by setting a span between 0 and 1, selecting an end portion of the normalized variance signal, and comparing values of the end portion of the normalized variance signal to a third threshold value,
wherein the at least one method is performed by the processor in real-time relative to receipt of the accelerometry data; and
a user interface configured to provide one or more outputs comprising at least one of audio or graphics,
the one or more outputs indicate a missing swallow for the accelerometry data based on one or more results of the at least one method, and the one or more outputs indicate that the accelerometry data was clipped from an end based on one or more results of the at least one method.

5. A device for screening swallowing safety and swallowing efficiency, the device comprising:
a processor configured to receive accelerometry data of throat vibrations, determine vibration signals of the accelerometry data along an anterior-posterior axis and a superior-inferior axis of the throat to be used in determining a spectrogram, and perform at least one method comprising (i) determining a signal variance of the accelerometry data as a function of time, as summed power over a specific frequency range of the spectrogram, and comparing the signal variance to a first threshold value,
the at least one method further comprising at least one additional method selected from the group consisting of (ii) determining a normalized variance signal from the spectrogram by setting a span between 0 and 1, selecting a beginning portion of the normalized variance signal, and comparing values of the beginning portion of the normalized variance signal to a second threshold value, and (iii) determining a normalized variance signal from the spectrogram by setting a span between 0 and 1, selecting an end portion of the normalized variance signal, and comparing values of the end portion of the normalized variance signal to a third threshold value, and
the at least one method further comprising (iv) determining a summed power spectral density of both the vibration signals along the anterior-posterior axis and the superior-inferior axis of the throat as an average of the spectrogram over a full duration or signal length relating to consumption of a single whole bolus and applying spectral entropy for the summed power spectral density (PSD) of both vibration signals along the anterior-posterior axis and the superior-inferior axis of the throat for comparison to a fourth threshold value,
wherein the at least one method is performed by the processor in real-time relative to receipt of the accelerometry data; and
a user interface configured to provide one or more outputs comprising at least one of audio or graphics,
the one or more outputs indicate a missing swallow for the accelerometry data based on one or more results of the at least one method, and the one or more outputs indicate that the accelerometry data comprises noise based on one or more results of the at least one method.

6. A device for screening swallowing safety and swallowing efficiency, the device comprising:
a processor configured to receive accelerometry data of throat vibrations, determine vibration signals of the accelerometry data along an anterior-posterior axis and a superior-inferior axis of the throat to be used in determining a spectrogram, perform at least one method selected from the group consisting of determining a signal variance of the accelerometry data as a function of time, as a summed power over a specific frequency range of the spectrogram, comparing the signal variance to a first threshold value, determining a normalized variance signal from the spectrogram by setting a span between 0 and 1, selecting a beginning portion of the normalized variance signal and comparing values of the beginning portion of the normalized variance signal to a second threshold value, selecting an end portion of the normalized variance signal and compare values of the end portion of the normalized variance signal to a third threshold value, and determining a summed power spectral density of both the vibration signals along the anterior-posterior axis and the superior-inferior axis of the throat as an average of the spectrogram over a full duration or signal length relating to consumption of a single bolus and apply spectral entropy for the summed power spectral density (PSD) of both the vibration signals along the anterior-posterior axis and the superior-inferior axis of the throat for comparison to a fourth threshold value,
wherein the at least one method is performed by the processor in real-time relative to receipt of the accelerometry data,
the processor further configured to react to the accelerometry data not exceeding the first, second, third and fourth threshold values by comparing the accelerometry data against preset classification criteria defined for each of swallowing safety and swallowing efficiency and classify each of a first plurality of swallowing events with a swallowing safety classification and a swallowing efficiency classification based at least partially on the comparing of swallowing data against the preset classification criteria; and
a user interface configured to provide one or more outputs comprising at least one of audio or graphics that identify the swallowing safety classification and the swallowing efficiency classification for each of the first plurality of swallowing events.

7. The device of claim 6 further comprising an accelerometer communicatively connected to the processor to provide the accelerometry data.

8. The device of claim 6, wherein:
the swallowing safety classification is identified from at least two predetermined swallowing safety classifications, and the swallowing efficiency classification is identified from at least two predetermined swallowing efficiency classifications;
the at least two predetermined swallowing safety classifications comprise a first swallowing safety classification indicative of a safe event and a second swallowing safety classification indicative of an unsafe event, and the at least two predetermined swallowing efficiency classifications comprise a first swallowing efficiency classification indicative of an efficient event and a second swallowing efficiency classification indicative of an inefficient event; and
the one or more outputs comprise at least one icon displayed on the user interface, at least a portion of the at least one icon is a first color for the first swallowing safety classification or a second color different than the first color for the second swallowing safety classification, at least a portion of the at least one icon is a third color for the first swallowing efficiency classification or a fourth color different than the third color for the second swallowing efficiency classification, and at least a portion of the at least one icon is a fifth color if any of the first, second, third and fourth threshold values were exceeded.

9. A method of screening swallowing safety and swallowing efficiency, the method comprising:
receiving, on a device comprising a processor, accelerometry data of throat vibrations for a swallowing event executed by an individual;
the throat vibrations comprising vibration signals determined, on the device, along an anterior-posterior axis and a superior-inferior axis of the throat to be used in determining a spectrogram;
performing, on the device, at least one method comprising (i) determining a signal variance of the accelerometry data as a function of time, as a summed power over a specific frequency range of the spectrogram, and comparing the signal variance to a first threshold value,
the at least one method further comprising at least one additional method selected from the group consisting of (ii) determining a normalized variance signal from the spectrogram by setting a span between 0 and 1, selecting a beginning portion of the normalized variance signal, and comparing values of the beginning portion of the normalized variance signal to a second threshold value, (iii) determining a normalized variance signal from the spectrogram by setting a span between 0 and 1, selecting an end portion of the normalized variance signal, and comparing values of the end portion of the normalized variance signal to a third threshold value, and (iv) determining a summed power spectral density of both the vibration signals along an anterior-posterior axis and a superior-inferior axis of the throat as an average of the spectrogram over a full duration or signal length relating to consumption of a single bolus and applying spectral entropy for the summed power spectral density (PSD) of both the vibration signals along the anterior-posterior axis and the superior-inferior axis of the throat for comparison to a fourth threshold value,
wherein the at least one method is performed by the processor in real-time relative to receipt of the accelerometry data; and
producing, from the device, one or more outputs comprising at least one of audio or graphics, and the one or more outputs indicate a missing swallow for the accelerometry data based on one or more results of the at least one method.

10. The method of claim 9 further comprising transmitting the first accelerometry data to the device from an accelerometer communicatively connected to the device.

11. The method of claim 9 further comprising the processor ceasing processing of corresponding accelerometry data in response to identification of the missing swallow.

12. A method of screening swallowing safety and swallowing efficiency, the method comprising:
receiving, on a device comprising a processor, accelerometry data of throat vibrations for a swallowing event executed by an individual;

the throat vibrations comprising vibration signals determined, on the device, along an anterior-posterior axis and a superior-inferior axis of the throat to be used in determining a spectrogram;

performing, on the device, at least one method comprising (i) determining a signal variance of the accelerometry data as function of time, as a summed power over a specific frequency range of the spectrogram, and comparing the signal variance to a first threshold value, and (ii) determining a normalized variance signal from the spectrogram by setting a span between 0 and 1, selecting a beginning portion of the normalized variance signal, and comparing values of the beginning portion of the normalized variance signal to a second threshold value, the at least one method further comprising at least one additional method selected from the group consisting of (iii) determining a normalized variance signal from the spectrogram by setting a span between 0 and 1, selecting an end portion of the normalized variance signal, and comparing values of the end portion of the normalized variance signal to a third threshold value, and (iv) determining a summed power spectral density of both the vibration signals along an anterior-posterior axis and a superior-inferior axis of the throat as an average of the spectrogram over a full duration or signal length relating to consumption of a single bolus and applying spectral entropy for the summed power spectral density (PSD) of both the vibration signals along an anterior-posterior axis and a superior-inferior axis of the throat for comparison to a fourth threshold value, wherein the at least one method is performed by the processor in real-time relative to receipt of the accelerometry data; and producing, from the device, one or more outputs comprising at least one of audio or graphics, and the one or more outputs indicate a missing swallow for the accelerometry data based on one or more results of the at least one method, and the one or more outputs indicate that the accelerometry data was clipped from a start based on one or more results of the at least one method.

13. The method of claim 12 further comprising the processor ceasing processing of corresponding accelerometry data in response to identification of the accelerometry data being clipped from the start.

14. A method of screening swallowing safety and swallowing efficiency, the method comprising:

receiving, on a device comprising a processor, accelerometry data of throat vibrations for a swallowing event executed by an individual;

the throat vibrations comprising vibration signals determined, on the device, along an anterior-posterior axis and a superior-inferior axis of the throat to be used in determining a spectrogram;

performing, on the device, at least one method comprising (i) determining a signal variance of the accelerometry data as function of time, as a summed power over a specific frequency range of the spectrogram, and comparing the signal variance to a first threshold value, the at least one method further comprising at least one additional method selected from the group consisting of (ii) determining a normalized variance signal from the spectrogram by setting a span between 0 and 1, selecting a beginning portion of the normalized variance signal, and comparing values of the beginning portion of the normalized variance signal to a second threshold value, and (iv) determining a summed power spectral density of both the vibration signals along an anterior-posterior axis and a superior-inferior axis of the throat as an average of the spectrogram over a full duration or signal length relating to consumption of a single bolus and applying spectral entropy for the summed power spectral density (PSD) of both the vibration signals along an anterior-posterior axis and a superior-inferior axis of the throat for comparison to a fourth threshold value, wherein the at least one method is performed by the processor in real-time relative to receipt of the accelerometry data, and the at least one method further comprising (iii) determining a normalized variance signal from the spectrogram by setting a span between 0 and 1, selecting an end portion of the normalized variance signal, and comparing values of the end portion of the normalized variance signal to a third threshold value; and producing, from the device, one or more outputs comprising at least one of audio or graphics, the one or more outputs indicate a missing swallow for the accelerometry data based on one or more results of the at least one method, and the one or more outputs indicate that the accelerometry data was clipped from an end based on one or more results of the at least one method.

15. The method of claim 14 further comprising the processor ceasing processing of corresponding accelerometry data in response to identification of the accelerometry data being clipped from the end.

16. A method of screening swallowing safety and swallowing efficiency, the method comprising:

receiving, on a device comprising a processor, accelerometry data of throat vibrations for a swallowing event executed by an individual;

the throat vibrations comprising vibration signals determined, on the device, along an anterior-posterior axis and a superior-inferior axis of the throat to be used in determining a spectrogram;

performing, on the device, at least one method comprising (i) determining a signal variance of the accelerometry data as function of time, as a summed power over a specific frequency range of the spectrogram, and comparing the signal variance to a first threshold value, the at least one method further comprising at least one additional method selected from the group consisting of (ii) determining a normalized variance signal from the spectrogram by setting a span between 0 and 1, selecting a beginning portion of the normalized variance signal, and comparing values of the beginning portion of the normalized variance signal to a second threshold value, and (iii) determining a normalized variance signal from the spectrogram by setting a span between 0 and 1, selecting an end portion of the normalized variance signal, and comparing values of the end portion of the normalized variance signal to a third threshold value, and the at least one method further comprising (iv) determining a summed power spectral density of both the vibration signals along an anterior-posterior axis and a superior-inferior axis of the throat as an average of the spectrogram over a full duration or signal length relating to consumption of a single bolus and applying spectral entropy for the summed power spectral density (PSD) of both the vibration signals along an anterior-posterior axis and a superior-inferior axis of the throat for comparison to a fourth threshold value, wherein the at least one method is performed by the processor in real-time relative to receipt of the accelerometry data; and producing, from the device, one or more outputs comprising at least one of audio or graphics, the one or more outputs indicate a missing swallow for the accelerometry data based on one or more results of the at least one method, and the one or more outputs indicate that the accelerometry data comprises noise based on one or more results of the at least one method.

17. The method of claim 16 further comprising the processor ceasing processing of corresponding accelerometry data in response to identification of the noise in the accelerometry data.

* * * * *